(12) United States Patent
Tolosa et al.

(10) Patent No.: US 10,379,047 B2
(45) Date of Patent: Aug. 13, 2019

(54) APPARATUS FOR DETECTING PH AND DISSOLVED OXYGEN

(71) Applicant: Scientific Industries, Inc., Bohemia, NY (US)

(72) Inventors: Michael Tolosa, Columbia, MD (US); William Chandler, Oakmont, PA (US); Douglas J. Koebler, Irwin, PA (US); Joseph G. Cremonese, Greensburg, PA (US); Brookman P. March, Casco, ME (US)

(73) Assignee: Scientific Industries, Inc., Bohemia, NY (US)

( * ) Notice: Subject to any disclaimer, the term of this patent is extended or adjusted under 35 U.S.C. 154(b) by 41 days.

(21) Appl. No.: 15/364,993

(22) Filed: Nov. 30, 2016

(65) Prior Publication Data

US 2018/0149593 A1    May 31, 2018

(51) Int. Cl.
| | | |
|---|---|---|
| *G01N 21/00* | (2006.01) | |
| *B01L 3/00* | (2006.01) | |
| *G01N 21/64* | (2006.01) | |
| *G01N 33/483* | (2006.01) | |

(52) U.S. Cl.
CPC ..... *G01N 21/6428* (2013.01); *G01N 33/4833* (2013.01); *G01N 2201/062* (2013.01)

(58) Field of Classification Search
CPC ......... G01N 2201/062; G01N 21/6428; G01N 33/4833
See application file for complete search history.

(56) References Cited

U.S. PATENT DOCUMENTS

| | | | | |
|---|---|---|---|---|
| 2008/0024779 | A1* | 1/2008 | Aasmul | G01J 3/4406 356/317 |
| 2011/0188053 | A1* | 8/2011 | Buermann | G02B 21/245 356/609 |

OTHER PUBLICATIONS

Ragupathy, V. et al., Non-Invasive Optical Sensor Based Approaches for Monitoring Virus Culture to Minimize BSL3 Laboratory Entry, Sensors, 2015, 14864-14870, vol. 15, MDPI, Basel, Switzerland.
Ge, X. et al., Low-Cost Noninvasive Optical CO2 Sensing System for Fermentation and Cell Culture, Biotechnology and BioEngineering, 2005, 329-334, vol. 89, No. 3, Wiley Peridocals, Inc.
Ge, X. et al., Validation of an Optical Sensor-Based High-Throughput Bioreactor System for Mammalian Cell Culture, Journal of Biotechnology, 2006, 291-306, vol. 122, Elsevier.com.

(Continued)

*Primary Examiner* — Nathan A Bowers
(74) *Attorney, Agent, or Firm* — Buchanan Ingersoll & Rooney PC

(57) ABSTRACT

Embodiments of a cell culture monitoring system are disclosed that may include a device having collimating and filtering components to elicit and detect fluorescence from a substrate located within a reaction vessel. The device may be used to detect changes in pH and dissolved oxygen levels in a liquid contained in the reaction vessel due to growth of living cells. Excitation light beams can be generated and collimated by a beam combiner and directed into the reaction vessel so as to be incident upon the substrate to cause the substrate to fluoresce. Some embodiments include use of expected wavelength offsets and shifted filters/mirrors to improve functionality and reduce space of device components.

16 Claims, 16 Drawing Sheets

(56) References Cited

OTHER PUBLICATIONS

Rao, G. et al., Disposable Bioprocessing: The Future Has Arrived, Biotechnology and BioEngineering, 2009, 348-356, vol. 102, No. 2, Wiley Periodicals, Inc.

Hanson, M.A., Comparisons of Optical pH and Dissolved Oxygen Sensors with Traditional Electrochemical Probes During Mammalian Cell Culture, 2007, 833-841, vol. 4, No. 4, Wiley Periodicals, Inc.

* cited by examiner

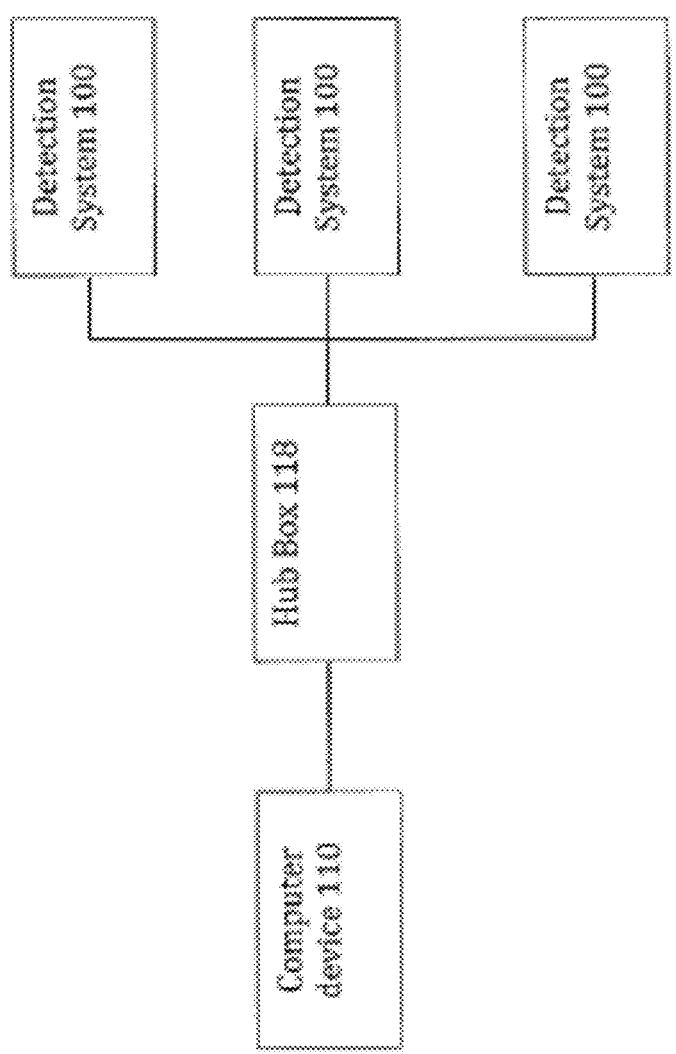

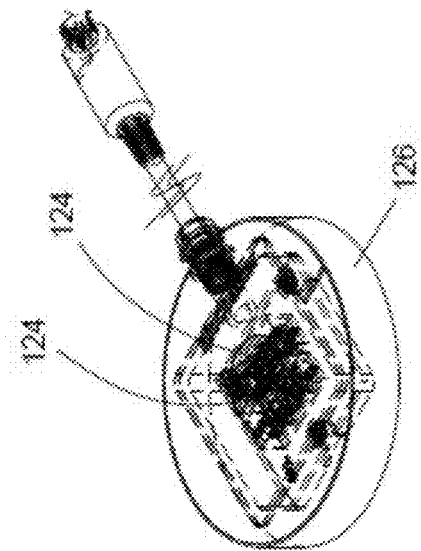
FIG. 2E
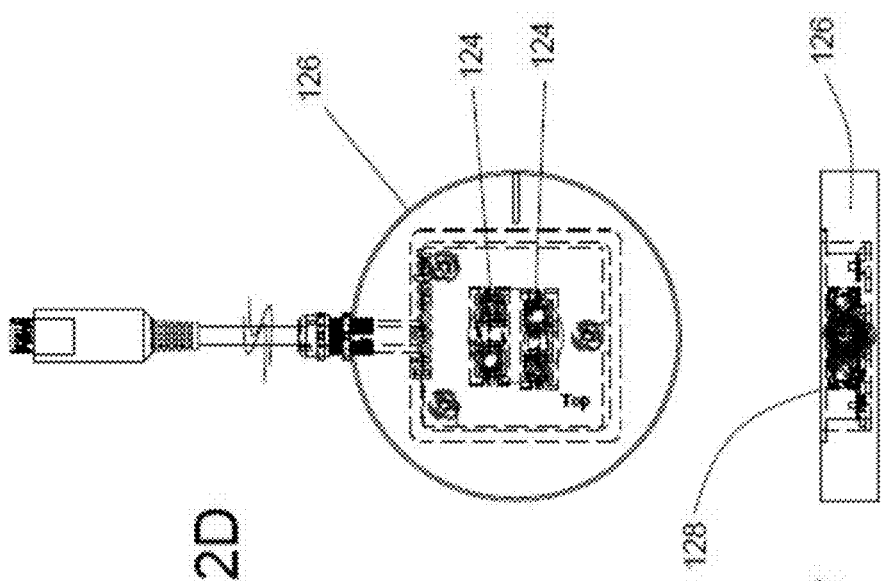
FIG. 2D
FIG. 2F

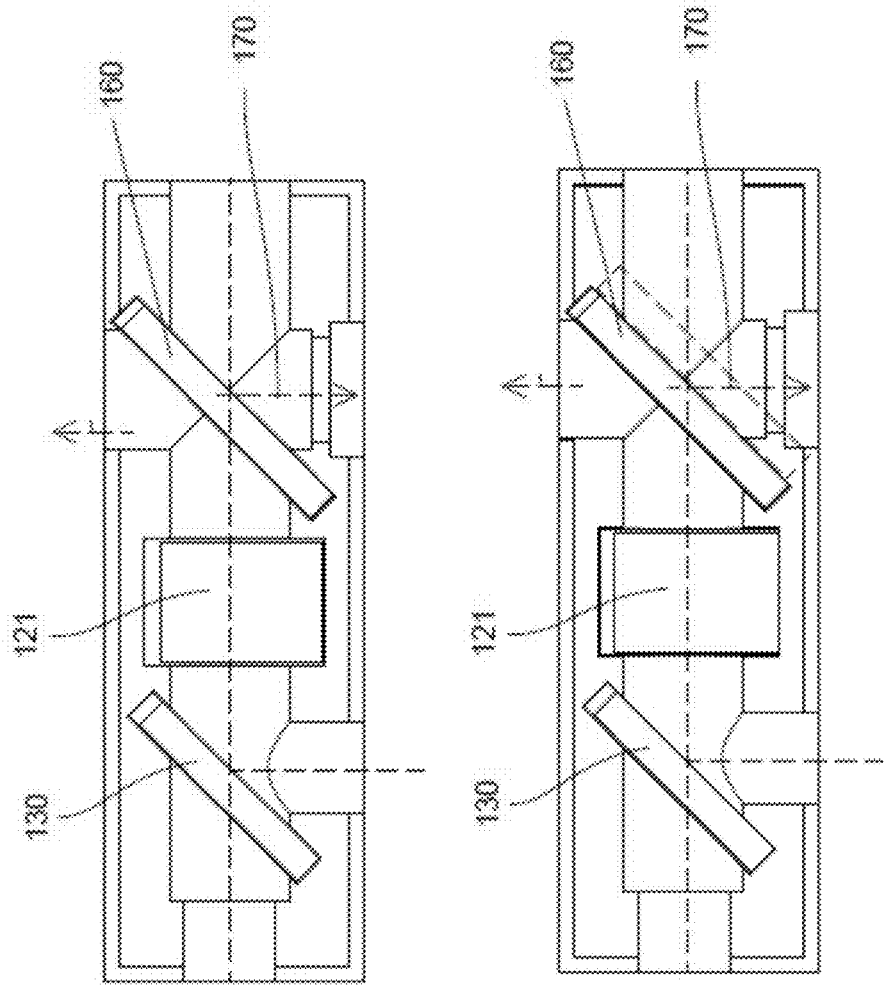

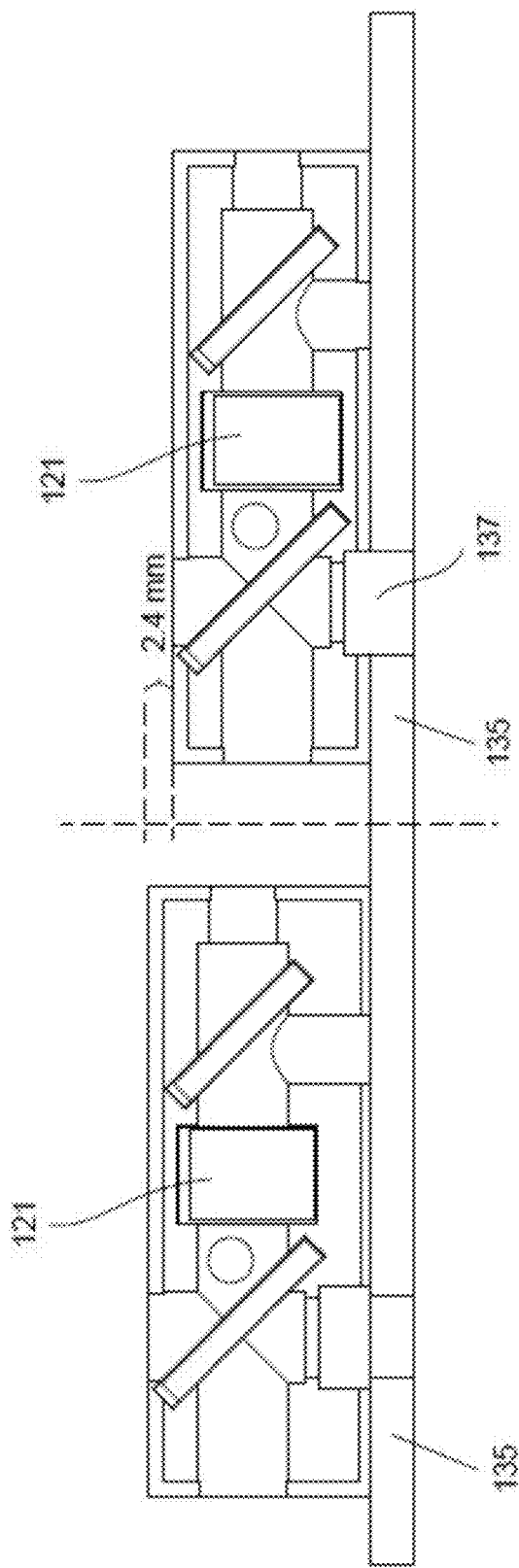

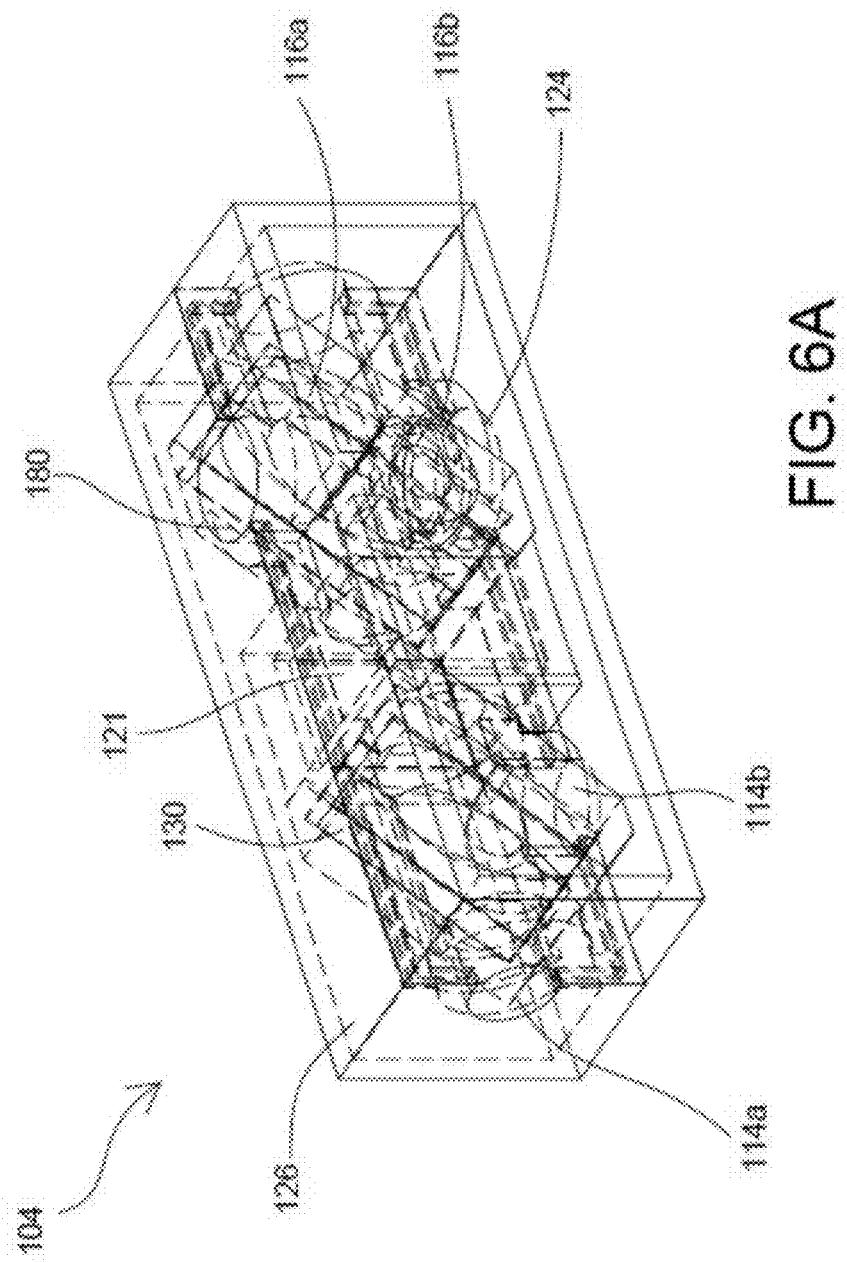

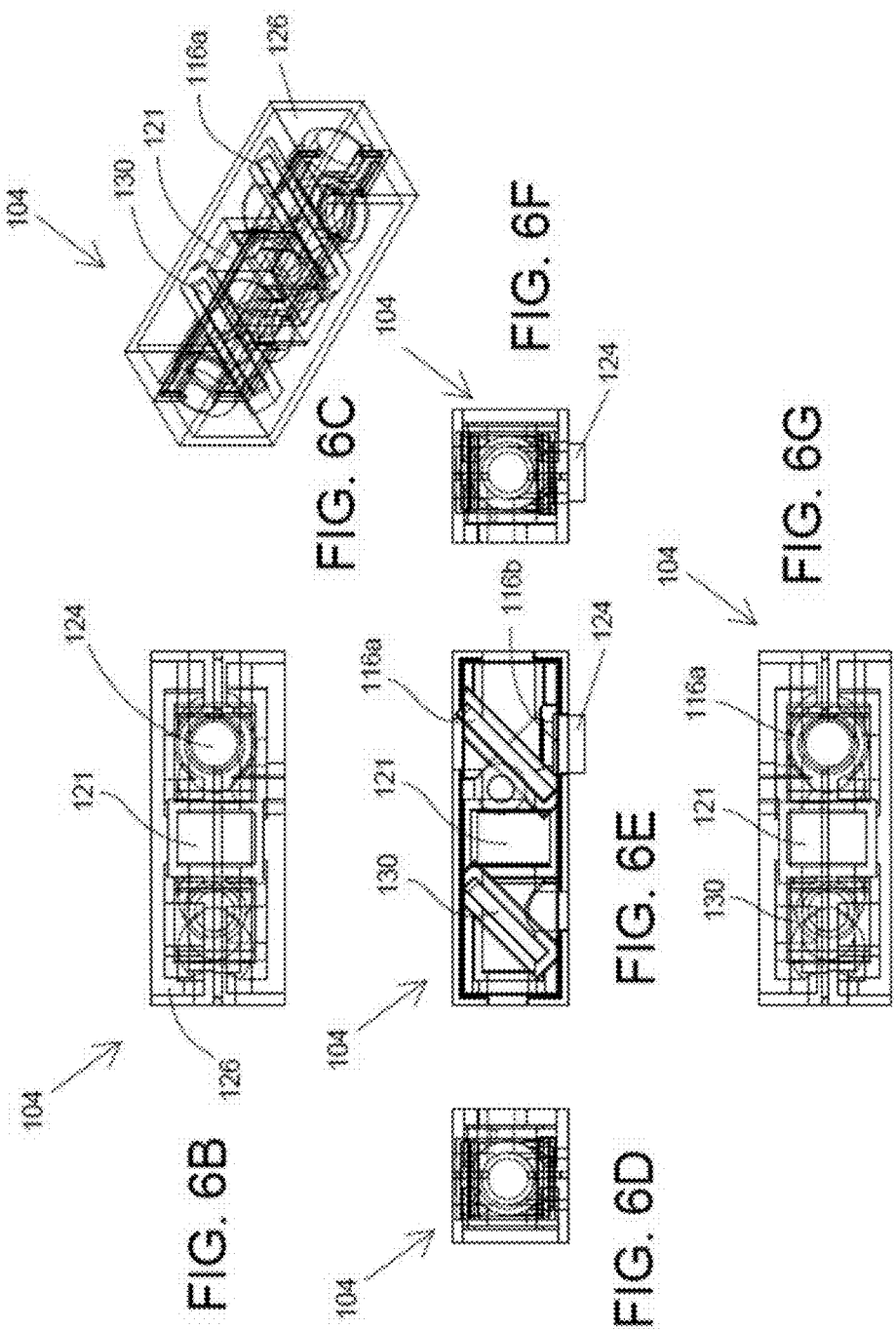

APPARATUS FOR DETECTING PH AND DISSOLVED OXYGEN

CROSS REFERENCE TO RELATED APPLICATIONS

This application claims the benefit of U.S. Provisional Application Ser. No. 62/262,512, filed on Dec. 3, 2015 and entitled "Apparatus for Detecting pH and Dissolved Oxygen," which is incorporated herein by reference in its entirety.

BACKGROUND OF THE INVENTION

Field of the Invention

Embodiments disclosed herein relate to systems and methods for detecting pH levels and/or dissolved oxygen levels in a liquid, which may include detecting changes in pH levels and/or dissolved oxygen levels in a culture sample due to growth of living cells contained in a reaction vessel.

Background of the Related Art

Traditional systems and methods of preparing, propagating, and monitoring cell cultures and/or viruses in cultures may be carried out in bio-safety laboratories. These systems tend to be in isolation due to safety reasons, and can be expensive or cost prohibitive. For example, physical entry into a bio-safety laboratory can involve extensive use of consumables, such as personal protective equipment. Yet, conventional techniques used to reduce the number of visits to the bio-safety laboratory tend to employ costly and complex equipment. Other techniques can involve devices that can be limited to one-time use, after which the devices may have to be discarded. Such systems and methods may reduce visits to a bio-safety laboratory, but they generally add complexity to monitoring processes.

Other out-of-laboratory systems can use electro-optics to monitor cell culture samples, yet they may require calibration of the position and/or angle of optical filters/mirrors of the system. Some may require calibration before, or even during, each use. Calibration in this manner can be time consuming, error prone, and/or require additional equipment, further adding to cost and complexity. Furthermore, such systems can be ill-conditioned, wherein small input changes (e.g., change in filter angle) can generate large output swings (e.g., resolution or sharpness of light).

BRIEF SUMMARY OF THE INVENTION

Measuring dissolved oxygen ("DO") and pH can provide a reliable approach to monitoring cell cultures via electro-optic techniques performed on cell culture samples. For instance, the biomass of growing cells can cause an increase in lactic acid within the cell growth medium (e.g., nutrient media), which can be due to an end-product of cell metabolism. An increase in lactic acid can cause a steady decrease of pH level in the cell growth medium. Furthermore, presence of DO can be an indicator of the health of the cell culture environment. Generally, optimal levels of DO in the cell growth medium provide a healthy environment for cell growth. Thus, pH levels and DO levels can be indicators of conditions within the cell culture. For example, DO saturation with a positive rate of change can be indicative of equilibrium, whereas decreasing level of pH below a certain amount or at a certain rate can be indicative of over-growth in the cell culture (i.e., may require a subculture). Other conditions that can be determined may include, but are not limited to, an onset of programmed cell death (e.g., apoptosis), growth toward equilibrium, deviations from equilibrium, etc.

Changes in DO levels and pH levels can be monitored through fluorescence techniques applied to a substrate within a cell growth medium. For example, a fluorescence-based patch containing fluorescent dye immobilized in a matrix can be placed within a reaction vessel containing the culture sample. Elicitation of fluorescence from chemicals within the patch can be performed, where emitted light due to induced fluorescence can be monitored via electro-optics and/or other system components located outside the reaction vessel. Thus, electro-optical measurements can be conducted on the cell culture in a minimally invasive and/or non-invasive manner. Furthermore, the patch can be structured such that emitted light due to the fluorescence can occur at different wavelengths, the wavelengths being a function of changes in DO levels and/or pH levels occurring within a growth medium. Such fluorescence techniques can be based on techniques disclosed in U.S. Pat. No. 6,673,532, filed Aug. 14, 2001, titled "Bioreactor and Bioprocessing Technique," which is incorporated herein by reference in its entirety. Any of those fluorescence techniques can be used by any of the embodiments of the detection system disclosed herein to detect pH levels and DO levels in culture cells.

In one embodiment, the detection system can include a specialized mini-fluorometer and calibrated sensor patches that respond to light excitation of very specific wavelength. The sensor patches, after fabrication and before use, can be calibrated to be read by an individual mini-fluorometer. Each set of optical patches, calibrated to a mini-fluorometer (i.e., a BioCoaster) can be used to generate a non-interchangeable system for reading. The reading can be for pH and dissolved oxygen, for example. The detection system can further include a beam combiner assembly, which may be designed so that specific optical filters and LED's may be used. Use of the specific optical filters and LED's can be such that every one is identical in response. Therefore, each beam combiner assembly can be interchangeable. The beam combiner assembly, including all required optical filters and LED's, may be installed on the digital sensor board to generate an embodiment of the mini-fluorometer. With the configuration of the detection system, it may not be necessary to calibrate each optical sensor patch to a specific BioCoaster each time the system is used. Instead, because of the design of the beam combiner assembly and in conjunction with the digital sensor board, optical sensor patches may be calibrated to a "GOLD COASTER" and the calibration will work with each and every other coaster produced using the beam combiner assembly.

An exemplary embodiment of a detection system may include a beam combiner assembly. The system can further include a fluorescence-based patch. A detector (e.g., photodiode) can be used to elicit and detect fluorescence emissions from chemicals of the patch. In some embodiments, the patch can be located within a culture sample environment of a reaction vessel. At least a portion of the reaction vessel can be transparent to form a reaction vessel window through which light generated by the beam combiner assembly can be directed and made incident upon the patch located within the reaction vessel. Emitted light, due to induced fluorescence from chemicals of the patch, can be made to be incident upon the detector. The detector can be located outside of the reaction vessel. In some embodiments, the beam combiner assembly can include the detector. Both the beam combiner assembly and the detector can be housed within a coaster shaped casing upon which the reaction vessel may be placed for monitoring.

Chemicals of the patch can be configured to fluoresce with a first expected wavelength of light as an indicator of a threshold level of DO in the culture sample and with a second expected wavelength of light as an indicator of a threshold level of pH in the culture sample. For example, it can be expected that a threshold level of DO within the culture sample would generate emitted light having a wavelength corresponding to red visible light when the patch within an environment of that culture sample is caused to fluoresce. It can be further expected that a threshold level of pH within the culture sample would generate emitted light having a wavelength corresponding to green visible light when the patch within an environment of that culture sample is caused to fluoresce.

In some embodiments, an expected offset between wavelengths of emitted light associated with DO threshold levels and pH threshold levels can be determined. For example, as emitted wavelength increases from green to red, a waveform phase offset occurs in the sine wave period because of a slight but accumulating system delay. The phase offset can be measured as an angle, considering that a complete sine wave period is 360 degrees with 90 degrees being the positive peak and 270 degrees being the negative peak. The phase offset angle can be stored in a memory of a computer device. This phase offset angle can be compared to a previously recorded positive peak that occurs when light passing through a red reflector (in the absence of a patch and absence of a culture sample) and detected. In other words, the light detected when the red reflector is in place can be used as the expected phase offset and stored in a computer device to be compared to when light emitted from a patch is detected. If a phase offset occurs as a result of the emission of a fluorescent signal, it may indicate that the emission frequency is at the red end of the calibrated range, and therefore must be emitting from a dissolved oxygen patch that responds to excitation by emitting at approximately 610 nm in wavelength. Embodiments of the detection system can be used to eliminate the need for an operator of the system to identify the sensor patch. Embodiments of the detection system may also, or alternatively, be used to eliminate manually determining which patch, or type of patch, is being used when measuring DO and/or pH. Thus, an expected difference in wavelength between visible red light and visible green light can be used by an embodiment of the detection system to automatically ascertain which patch (a DO patch or a pH patch) is generating emitted light due to induced fluorescence. In some embodiments, the detection system can automatically determine which patch is being used and can adjust accordingly. Such techniques can further eliminate manually entering patch data corresponding to a type of patch into a culture monitoring system, which can save time and reduce error.

As by way of example, if the detection system detects emitted light at or near an expected red light for DO, then the detection system can automatically ascertain that emitted light from the reaction vessel is radiating from a DO patch. If the detection system detects emitted light that is not at or near an expected red light for DO, then the detection system can automatically ascertain that emitted light from the reaction vessel is radiating from a pH patch.

In some embodiments, the expected offset can be determined and programmed into the detection system by use of a red reflector and/or a red light emitting diode ("LED"). For example, prior to use of the detection system, red light from a red reflector and/or red LED can enable the detection system to register the red light as the expected offset. The expected offset can be used with the detection system by ascertaining which patch is radiating emitted light based on whether emitted light at or near the expected offset is detected. Coding an expected offset for each patch and/or set of patches can be performed before being employed within the reaction vessel to monitor culture samples. By coding, or at least marking, the patch or set of patches with the expected offset for that patch or set of patches, a user can then employ the patches by being provided the code. For example, a user can be provided with a code corresponding to an expected offset of the patch. The code can be used to inform the computer device at which wavelength the expected offset is set for the patch.

Some embodiments can include a dichroic filter/mirror arrangement with a cylindrical filter and/or mirror and/or a shifted filter and/or mirror. Using a shifted mirror/filter arrangement can facilitate use of the cylindrical filter so as to allow the cylindrical filter to protrude into a circuit board to which it may be attached. The filter may also extend below the base of the circuit board. This may enable reducing a height of the circuit board block that used to house the mirror/filter arrangement. In some embodiment, the detection system and the reaction vessel may be placed within an incubator, thus reducing a volume of space that the circuit board occupies may be a desired aspect of a detection system.

Using optical measurements with shifted filter/mirror arrangements and expected offsets within the detection system can facilitate miniaturization of system components and enable monitoring DO levels and pH levels with improved sensitivity, as compared to conventional detection systems. Some embodiments can facilitate monitoring DO levels and pH levels in a minimally invasive and/or non-invasive manner. Embodiments of the disclosed detection system and a method of use can further facilitate carrying out cell cultures remotely by significantly reducing and/or eliminating visits to a bio-safety laboratory. For example, carrying out cell cultures with embodiments of the system can be performed for up to twenty-one days without a visit to a bio-safety laboratory. Monitoring can be performed without calibration of system components (e.g., without calibrating filter/mirror positions and/or angles) that may otherwise have to be performed if conventional systems and methods were to be employed.

In an exemplary embodiment a cell culture monitoring system can include a beam combiner assembly configured to generate at least one excitation light beam for inducing fluorescence. The system can further include at least one patch configured to be placed within a reaction vessel and to generate emitted light due to the induced fluorescence by the at least one excitation light beam. The system can further include a detector to detect the emitted light. In some embodiments, the at least one patch may be associated with an expected offset. The expected offset may be an expected wavelength of the emitted light corresponding to the at least one patch generating the emitted light while in presence of dissolved oxygen. In some embodiments, the detector can be configured to detect a wavelength of emitted light relative to the expected offset.

The system can further include a hub box that may be in connection with at least one beam combiner assembly that can be configured to receive data representative of detected emitted light from the detector and to transmit the emitted light data to at least one computer device. The computer device may be configured to determine a type of the at least one patch based on the emitted light data and the expected offset.

In some embodiments, the at least one patch can further include at least one of a pH patch and a dissolved oxygen patch. The pH patch may be impregnated with chemicals to generate a first wavelength upon induced fluorescence. The dissolved oxygen patch may be impregnated with chemicals to generate a second wavelength upon induced fluorescence. An intensity of the emitted light from the dissolved oxygen patch may increase as a level of dissolved oxygen concentration that the dissolved oxygen patch is exposed to decreases. In some embodiments, the at least one patch can include a cellulous-based filter paper with a silicon adhesive backing. In some embodiments, the beam combiner assembly can generate the at least one excitation light beam via a light emitting diode ("LED"). The beam combiner assembly can further include a band filter to generate a bandwidth of excitation light.

In some embodiments, the beam combiner assembly can further include at least one illumination source, a beam combiner, a first filter/mirror arrangement, a second filter/mirror arrangement, and the detector. In some embodiments, the at least one excitation light beam can be caused to be sent through the beam combiner to be combined with another excitation light beam. The combined excitation light beam may be collimated and made to be coaxial. The combined excitation light beam may be further directed to be incident on the at least one patch within the reaction vessel. In some embodiments, the combined excitation light beam can induce the emitted light from the at least one patch due to induced fluorescence. In some embodiments, the emitted light being incident upon both the first filter/mirror arrangement and the second filter/mirror arrangement may be detected by the detector. In some embodiments, the beam combiner assembly can be housed within a circuit board block. A filter of at least one of the first filter/mirror arrangement and the second filter/mirror arrangement can be seated within a base of the circuit board block. A mirror of at least one of the first filter/mirror arrangement and the second filter/mirror arrangement can be shifted with respect to its associated filter.

In another exemplary embodiment, a cell culture monitoring system can include a beam combiner assembly configured to generate at least two excitation light beams for inducing fluorescence. The beam combiner assembly can further include at least one illumination source, a beam combiner, a first filter/mirror arrangement, a second filter/mirror arrangement, and a detector. In some embodiments, the at least two excitation light beams can be combined by the beam combiner to be collimated and coaxial. The combined excitation light beam may be directed to be incident on a patch within a reaction vessel. The combined excitation light beam can induce emitted light from the patch due to induced fluorescence. The emitted light may be directed to be incident upon the first filter/mirror arrangement and the second filter/mirror arrangement to be detected by the detector. The beam combiner assembly may be housed within a circuit board block. A filter of at least one of the first filter/mirror arrangement and the second filter/mirror arrangement can be seated within a base of the circuit board block. A mirror of at least one of the first filter/mirror arrangement and the second filter/mirror arrangement can be shifted with respect to its associated filter.

In some embodiments, the patch can be associated with an expected offset. The expected offset can be an expected wavelength of the emitted light corresponding to the patch generating the emitted light while in presence of dissolved oxygen. The detector may be configured to detect a wavelength of emitted light relative to the expected offset. The system can further include a hub box in connection with at least one beam combiner assembly that may receive data representative of detected emitted light from the detector and transmit the emitted light data to at least one computer device. The computer device can be configured to determine a type of the patch based on the emitted light data and the expected offset.

In some embodiments, the patch can include at least one of a pH patch and a dissolved oxygen patch. The pH patch may be impregnated with chemicals to generate a first wavelength upon induced fluorescence. The dissolved oxygen patch can be impregnated with chemicals to generate a second wavelength upon induced fluorescence. An intensity of the emitted light from the dissolved oxygen patch can increase as a level of dissolved oxygen concentration that the dissolved oxygen patch is exposed to decreases. In some embodiments, the patch can include a cellulous-based filter paper with a silicon adhesive backing. In some embodiments, the beam combiner assembly can generate the at least two excitation light beams via at least one light emitting diode. At least one band filter can be used to generate a bandwidth of excitation light for each excitation light beam.

In an exemplary implementation, a method of monitoring cell cultures can include placing an empty reaction vessel without a patch inline with an excitation path of a culture monitoring system such that there is no reflected light reaching a detector of the culture monitoring system. The method can further include placing a red reflector against a beam combiner window of a beam combiner assembly. The method can further include placing the reaction vessel adjacent the beam combiner assembly and between the beam combiner assembly and the red reflector. The method can further include generating at least two excitation light beams so as to detect red light by the detector. The method can further include determining an expected offset via the detected red light. The method can further include recording and encoding the expected offset. The method can further include affixing at least one of a pH patch and a dissolved oxygen patch to an inside of the reaction vessel with the reaction vessel being empty otherwise. The method can further include placing a cell culture within the reaction vessel for which the expected offset for the at least one patch associated therewith has been calculated. The method can further include removing the red reflector from the beam combiner assembly. The method can further include combining the at least two excitation light beams to be collimated and coaxial, the combined excitation light beams being made to be incident upon the at least one pH patch and the at least one dissolved oxygen patch. The method can further include directing the emitted light from the at least one pH patch and the at least one dissolved oxygen patch to be incident upon a pass filter and further incident upon the detector. The method can further include using the detected emitted light and the encoded expected offset to determine if the reaction vessel contains the pH patch or the dissolved oxygen patch.

The method can further include associating the at least one pH patch and the at least one dissolved oxygen patch with the expected offset via a code. The method can further include using the detected emitted light and the encoded expected offset to determine a type of patch for a plurality of patches, forming a set of patches associated with an expected offset code. The method can further include generating the red light via a light emitting diode incorporated into the beam combiner assembly as opposed to using a red reflector. The method can further include monitoring the cell culture within the reaction vessel without calibration of filter angle and without calibration of filter positioning of a filter within the beam combiner assembly. The method can further include generating the at least two excitation light beams via at least one light emitting diode and generating a bandwidth of excitation light for the at least two excitation light beams. The method can further include adjusting a gain of the at least one light emitting diode, generating a specific intensity each for the at least two excitation light beams. The method can further include monitoring the emitted light by a computer device to cause a computer device to influence electrical, mechanical, and optical components of a cell culture monitoring system.

While these potential advantages are made possible by technical solutions offered herein, they are not required to be achieved. Embodiments of the presently disclosed system and method can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following drawings, in which:

FIG. 1B shows an embodiment of a detection system in connections with a computer device.

FIGS. 2D-2F, are various views of an embodiment of a beam combiner assembly with a dual detector that may be used with an embodiment of detection system.

FIGS. 4A-4B are side cross-sectional views of embodiments of beam combiner assemblies showing a non-shifted filter/mirror arrangement and a shifted filter/mirror arrangement, respectively, that may be used with an embodiment of detection system.

FIGS. 5A-5B shows variations in height between an embodiment of a circuit board block with a non-cylindrical filter and non-shifted mirror, and an embodiment of a circuit board block with a cylindrical filter and a shifted mirror, respectively, that may be used with an embodiment of detection system.

FIGS. 6A-6G show various views of an embodiment of a beam combiner assembly with an exemplary offsetting generator that may be used with an embodiment of detection system.

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Figure 1A:
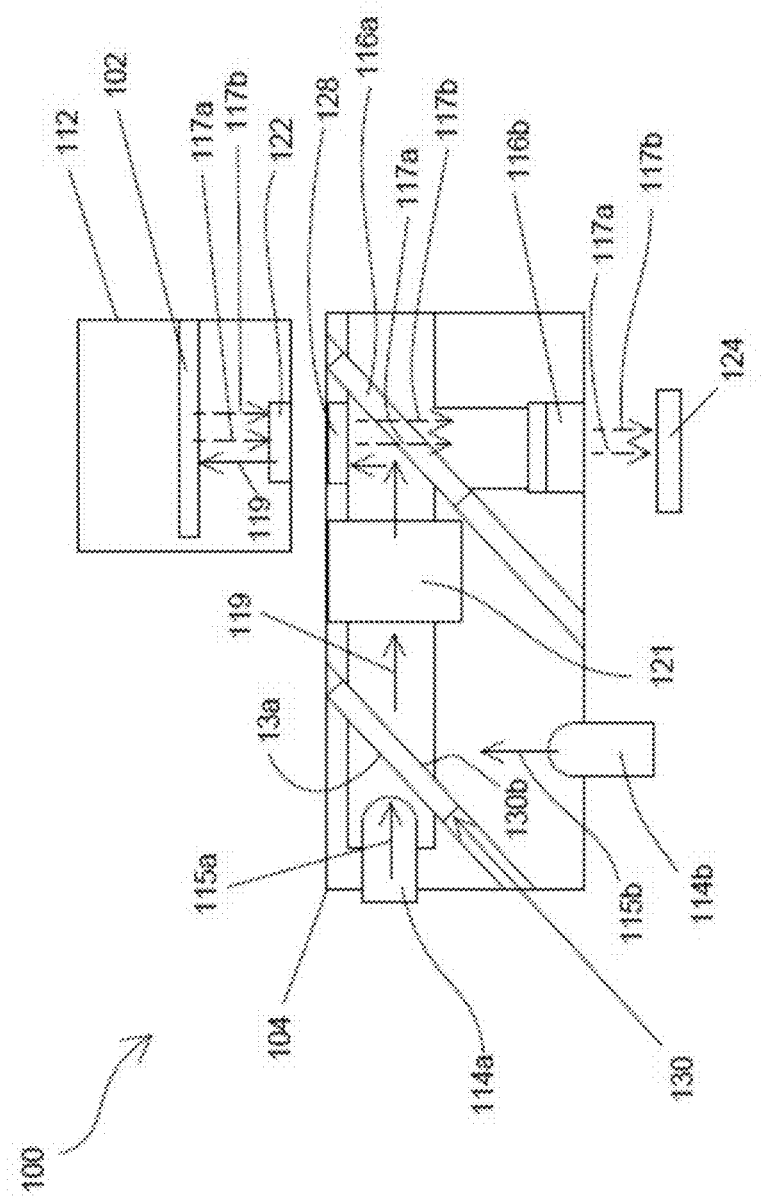
FIG. 1A shows a block diagram of an embodiment of an exemplary detection system.
Figure 2B:
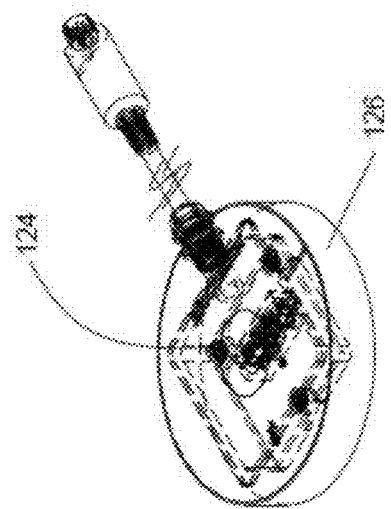
FIGS. 2A-2C are various views of an embodiment of a beam combiner assembly with a single detector that may be used with an embodiment of detection system.
Figure 2A:
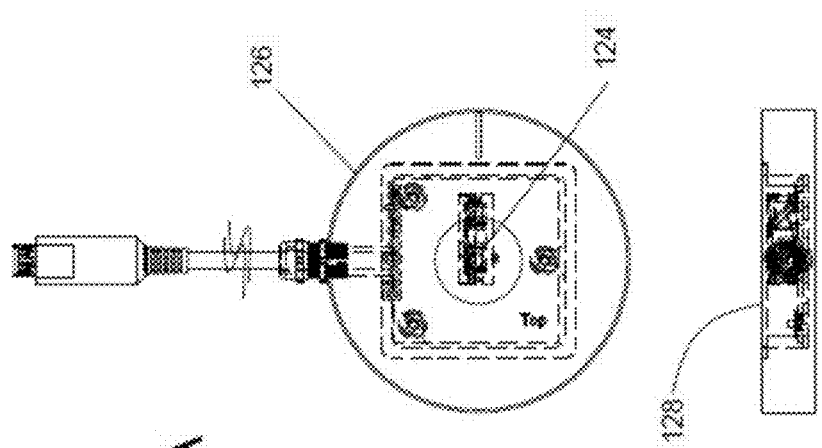
Figure 2C:
Figure 3B:
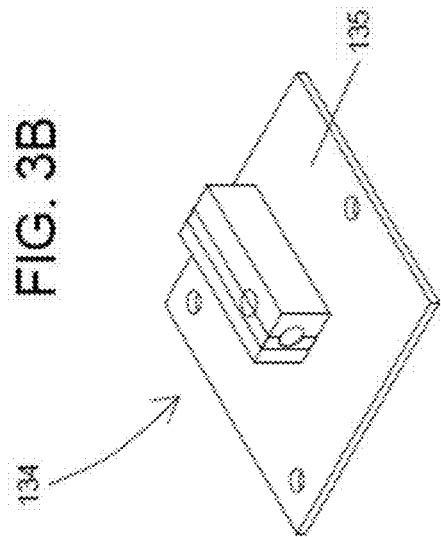
FIGS. 3A-3C are various view of an embodiment of a circuit board block with a single detector that may be used with an embodiment of detection system
Figure 3A:
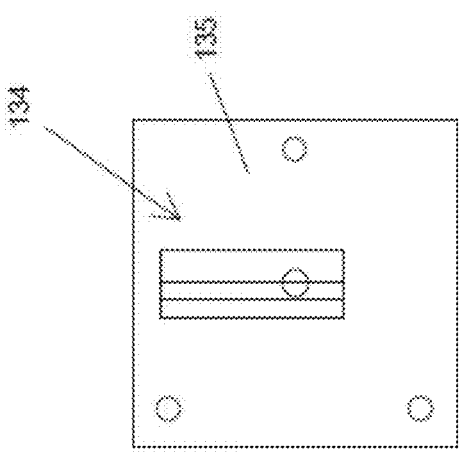
Figure 3C:
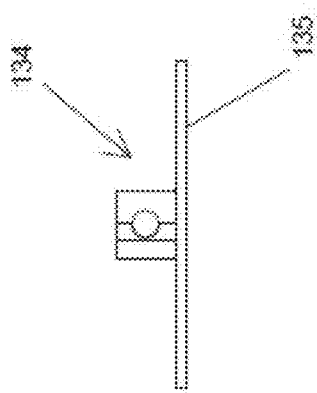
Figure 3E:
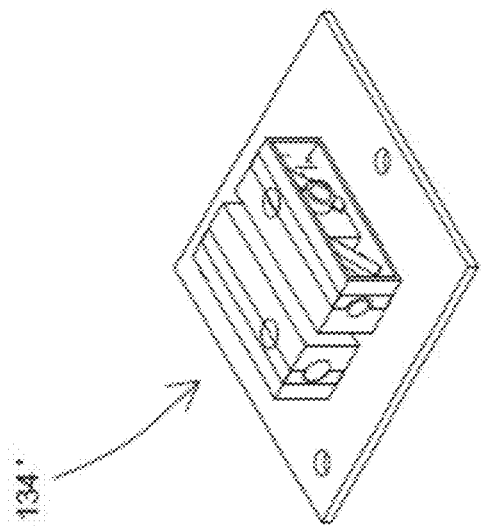
FIGS. 3D-3F are various view of an embodiment of a circuit board block with a dual detector that may be used with an embodiment of detection system.
Figure 3D:
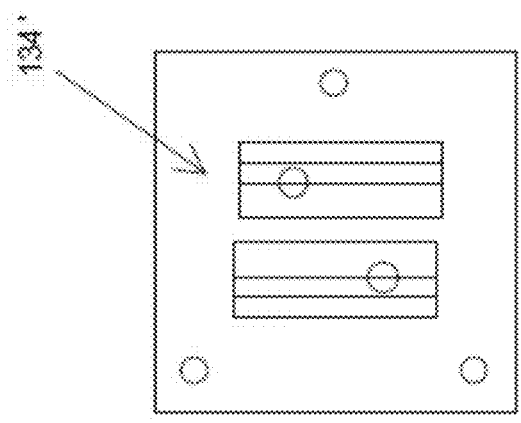
Figure 3F:
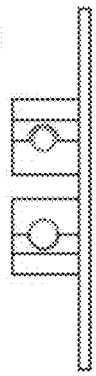

Referring to FIGS. 1A-B, a detection system 100 can include a fluorescent-based patch 102 and a beam combiner assembly 104. Some embodiments can include at least one computer device 110 in connection with the detection system 100 (see FIG. 1B). The computer device 110 can be programmed to run software generating user interfaces 108 (see FIGS. 8A-8B) that may be displayed via at least one computer device 110. The computer device 110 may be part of a computer system 106 (see FIG. 10). Some embodiments include use of a patch 102. The patch 102 may be can be placed into a reaction vessel 112 containing a culture sample to be monitored. The beam combiner assembly 104 can include at least one illumination source 114a, 114b, optical filters/mirrors 116a, 116b, and/or other optoelectronics, which can be used to generate excitation light beams 115a, 115b and detect emitted light 117a, 117b that may be induced by fluorescence. A hub box 118 can be used to communicatively and operably associate the computer device 110 to at least one beam combiner assembly 104. The hub box 118 can be a data acquisition card, for example. Use of a hub box 118 can facilitate data transmission between the computer device 110 and each beam combiner assembly 104.

In some embodiments, at least one hub box 118 can be used to acquire data from a plurality of reaction vessels 112. In further embodiments, the hub box 118 can be used to determine a life of the patch 102, which may be defined as the time frame by which the patch 102 can effectively fluorescence. This can be done by acquisitioning code data from the patch 102. For instance, the code can be manufacturing data, for example, that may be transmitted to the computer device 110 to calculate expiration times. Other data, such as an expected offset of a patch 102 can be encoded within the code that is associated with the patch 102. This code can include information such as a date of manufacture of the patch 102, a date at which the expected offset was determined, a date the patch 102 was packaged, etc. Chemicals within the patch 102 can photo-bleach after a statistically pre-determined use has elapsed (e.g., imparting excitation light beams on the patch 102 every fifteen seconds for ninety days can cause chemicals impregnated into the patch 102 to fail to effectively fluoresce and radiate emitted light), and thus the code can include an expected expiration date based on the date of manufacture. In another embodiment, the computer device 110 can calculate the expected expiration date based on such data.

The code can further include a "calibration" date, which can include a pre-set time period after which a date the expected offset was determined. In some embodiments, the "calibration" date can indicate when the expected offset should be determined again. For example, if the date the expected offset is determined by a computer device 110 to be greater than six months from a current date of use, then the computer device 110 may transmit a signal to the hub box 118 indicating that the patch 102 should be "calibrated." The hub box 118 can further be structured to have at least one useful life and/or calibration light indicator, indicating gradations of approaching expiration and/or calibration dates for the patch 102. For example, a green indicator light can be used to indicate that the patch 102 has at least two months before replacement and/or calibration. An amber light can be used to indicate that the patch 102 has less than one month before replacement and/or calibration. A red light can be used to indicate that the patch 102 has less than one week before replacement and/or calibration. Other indicator light schemes and/or time frames can be used.

In some embodiments, at least one computer device 110 can be communicatively and operably associated with a computer system 106 via a computer network. (See FIG. 10). In one embodiment, the hub box 118 can enable collection of data associated with each reaction vessel 112 being monitored and enable command data to be transmitted to each beam combiner assembly 104 from a user of the computer device 112 via the user interface 108 (see FIGS. 8A-B) of the detection system 100. In some embodiment, each reaction vessel 112 and/or computer device 110 can be in connection with the hub box 118 via a hardwire and/or via wireless connection. The hardwire connection can be can be achieved via a USB cable, other data cable, coaxial cable, T1 cable, or other network cable. The wireless connection can be achieved via transmitter, receiver, and/or transceiver units, which may be in connection through a communications network. 148. Embodiments including the computer system 106 can facilitate data transfer to and from a plurality of computer devices 110, hub boxes 118, and/or reaction vessels 112. Controllers and actuators can be used to influence pumps, photodiodes, etc. that may be used with embodiments of the detection system 100 via command data transmitted through the computer device(s) 110. In some embodiments, the computer device 110 can be programmed to generate command data automatically based on algorithms, which can be based on reaction vessel data being collected, as well as command data entered by a user via a user interface 132', 132" of the computer device 110 in communication with the detection system 100.

At least a portion of a reaction vessel 112 can be transparent to form a reaction vessel window 122. In some embodiments, light 115a, 115b generated by a beam combiner assembly 104 can be directed to be incident upon a patch 102 located within a reaction vessel 112. The reaction vessel window 122 can be further configured to allow emitted light 117a, 117b from induced fluorescence of the patch 102 to be passed through the reaction vessel 112 so that it can be incident upon a detector 124 that may be located outside of the reaction vessel 112, which may include being located on an outside surface of the reaction vessel 112 or on an outside surface of the beam combiner assembly 104. The detector 124 can be a device that is configured to detect various emitted light 117a, 117b based on wavelength and/or intensity. In some embodiments, the detector 124 can be a photodiode. In further embodiments, the detector 124 can also include a processor configured to convert the detected light into emitted light data, which can be representative of the light being detected. The detector 124 may also be configured to transmit the emitted light data to another component of the system 100.

The reaction vessel 112 can be a structure configured to support a cell culture. Any portion of the reaction vessel 112 can be opaque, translucent, or transparent. For example, the reaction vessel 112 may be a plastic or glass flask (e.g., T-75 $cm^2$ flask). The patch 102 can be positioned within the reaction vessel 112 to be exposed to a culture cell environment so that changes in DO levels and/or pH levels within the reaction vessel 112 can be monitored by chemical reactions of the patch 102 that are dependent upon the DO levels and/or the pH levels.

Figure 7:
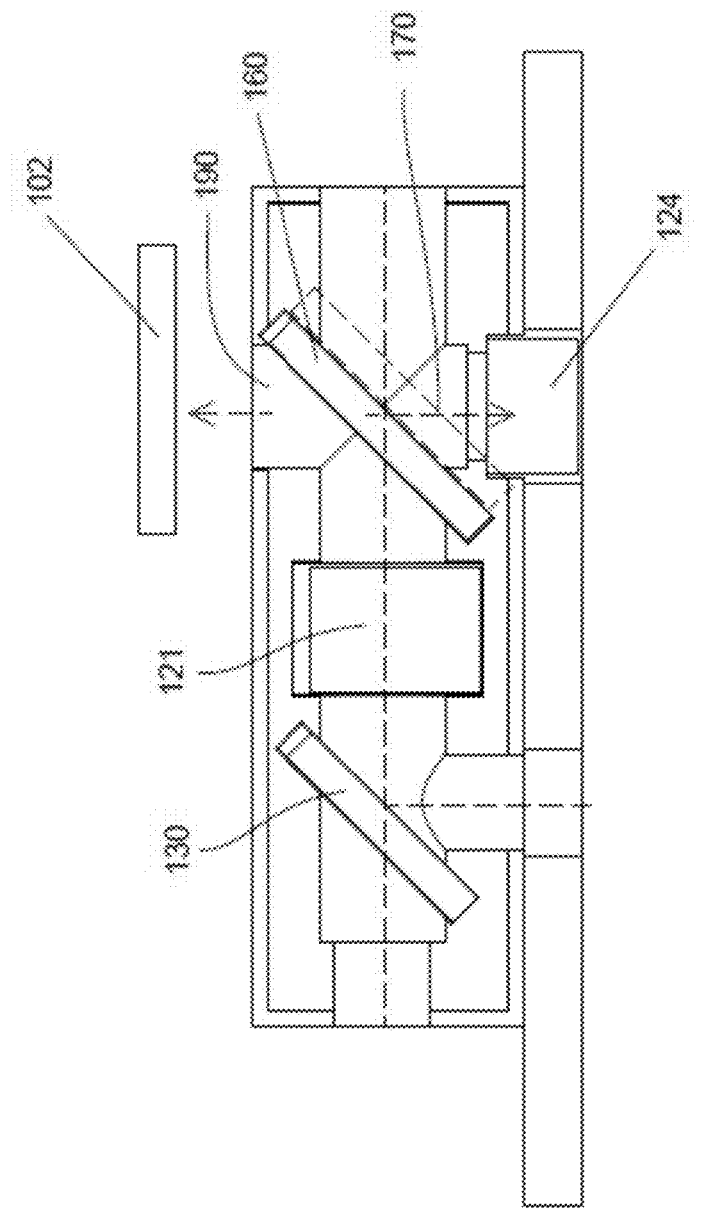
FIG. 7 is a side view of an exemplary beam combiner assembly with a widened beam combiner window that may be used with an embodiment of detection system.

Referring to FIGS. 2A-F, the beam combiner assembly 104 can include the detector 124. In some embodiments, both the beam combiner assembly 104 and the detector 124 can be housed within a casing 126. The casing 126 can be configured to allow the reaction vessel 112 to be placed thereon or adjacent thereto. In some embodiments, the casing 126 can be coaster shaped. For example, the casing 126 can be a planar puck-like object, which may have a profile that is round, square, triangular, etc. In one embodiment, the casing 126 can include a rigid puck-like body with a beam combiner assembly window 128 through which excitation and/or emitted light can travel. The beam combiner assembly window 128 may include an aperture 190 (see FIG. 7) within a body of a casing 126. The aperture 190 may further include a transparent cover and/or lens to enable transmission of excitation 115a, 115b and/or emitted light 117a, 117b, but prevent foreign objects from entering into a casing 126. For example, the transparent cover may be a filter configured to permit certain wavelengths of light and/or bands of wavelengths to be transmitted therethrough. In at least one embodiment, the beam combiner assembly window 128 can be structured with a widened aperture so as to facilitate more excitation and/or emitted light to pass there-through (see FIG. 7). Some embodiments can include a beam combiner assembly 104 with a single detector 124 or single sensing unit (see FIGS. 2A-C) and some embodiments can include a plurality of detectors 124 or a plurality of sensing units (see FIG. 2D-F).

The beam combiner assembly 104 may house illumination sources, filters, mirrors, detectors, and other electro-optics. Generation of excitation light beams 115a, 115b may be achieved through use of at least one light emitting diode ("LED"), laser, or other illumination source 114a, 114b capable of generating coherent light and/or light within a very narrow bandwidth of wavelengths. Direction of excitation light beams 115a, 115b and/or emitted light 117a, 117b within a beam combiner assembly 104 can be achieved through use of waveguides, reflectors, refractors, etc.

In at least one implementation, the beam combiner assembly 104 can be positioned outside a reaction vessel 112 with a reaction vessel 112 placed adjacent thereto (e.g., placed on top) so that excitation light beams 115a, 115b generated by a beam combiner assembly 104 can be incident on the patch 102 within a reaction vessel 112 when caused to transmit through the reaction vessel window 122. For example, the beam combiner assembly 104 can facilitate resting a beam combiner assembly 104 on a flat, stable surface, which may enable placing a reaction vessel 112 on top and adjacent the beam combiner assembly window 128. For example, the reaction vessel 112 can be placed on top of the beam combiner assembly 104, where at least one excitation light beam 115a, 115b can be directed through a bottom of the reaction vessel 112 to be incident upon the patch 102 that may be attached to an inside surface of a reaction vessel 112.

The system 100 can include a plurality of beam combiner assemblies 104. Whether there is one beam combiner assembly 104 or more than one, each beam combiner assembly 104 can be placed into electrical connection with an electrical power source to enable operation of the illumination sources 114 and/or other electro-optics. Any beam combiner assembly 104 can be further placed into electrical connection with the hub box 118. The hub box 118 can be separately placed into electrical connection with an electrical power source. As excitation light beams 115a, 115b are generated and directed to the patch 102 to induce emitted light 117a, 117b due to fluorescence, the emitted light 117a, 117b can be detected by the detector(s) 124. Excitation light beams 117a, 117b can be generated in a controlled manner via the computer device 110 (e.g., via algorithms and/or command data from users of a computer device). Emitted light data can be generated by the detector 124 and transmitted via the hub box 118 to the computer device 110 for data processing, data manipulation, and/or data analysis. In some embodiments, the detector 124 can include a processor to facilitate digitization of the emitted light 117a, 117b and transmission of digitized signals to the hub box 118 and/or the computer device 110.

In the non-limiting exemplary embodiment shown in FIG. 1, an exemplary beam combiner assembly 104 can include at least one illumination source 114a, 114b, at least one filter/mirror arrangement 116a, 116b, at least one beam combiner 130, and at least one detector 124. The first illumination source 114a can generate a first excitation light beam 115a (e.g., a violet light beam at or near 405 nm). The second illumination source 114b can generate a second excitation light beam 115b (e.g., blue light beam at or near 470 nm). Each of the first and second excitation light beams 115a, 115b can be directed toward the beam combiner 130. The beam combiner 130 can be positioned (e.g., at a desired angle incident to each of the first and second excitation light beam 115a, 115b) and structured (e.g., dichroic filter/mirror) to pass one of the excitation light beams 115a, 115b and reflect another excitation light beam 115a, 115b at an angle so that both excitation light beams 115a, 115b are coaxial and collimated in a single direction. For example, a violet light beam 115a can be directed toward a beam combiner 130 at a given angle (e.g., 45-degree angle), incident upon a first surface 130a of the beam combiner 130, whereas a blue light beam 115b can be directed toward the beam combiner 130 at a given angle (e.g., 45-degree angle), incident upon a second surface 130b of the beam combiner 130. The first surface 130a of a beam combiner 130 can be a light filter (e.g., a dichroic filter), and the second surface 130b of the beam combiner 130 can be a reflector (e.g., a dichroic mirror). The violet light beam 115a can be allowed to pass through while the blue light beam 115b may be reflected and caused to travel in a same direction as the violet light beam 115a, thereby generating a combined violet-blue light beam 119 that is collimated and coaxial. Other filters and/or mirror configurations, as well as angles of incidence and reflection can be used for the beam combiner 130. In some embodiments, excitation light beams 115a, 115b can be made to refract or even diffract from components of the beam combiner 130 to generate a combined light beam 119 comprising the first and second excitation light beams 115a, 115b that is collimated and coaxial.

The combine light beam 119 can be directed toward the first filter/mirror arrangement 116a, which may be a dichroic filter/mirror. The combined light beam can be further sharpened before being incident upon the first filter/mirror arrangement 116a by a beam sharpener 121. The first filter/mirror arrangement 116a can reflect the combined light beam 119 and cause it to travel through the beam combiner assembly window 128. The combined light beam 119 can then be directed through the reaction vessel window 122 to be incident upon the patch 102 that may be located within the reaction vessel 112. The combined light 119 being incident upon the patch 102 can induce fluorescence of chemicals within the patch 102. This may cause at least one emitted light 117a, 117b to be generated and radiate from the patch 102. The emitted light 117a, 117b be can at a certain wavelength, which may depend on the pH level and/or DO level of the environment within which the patch 102 is exposed. For example, with a combined light beam 119 comprising violet and blue light, chemicals impregnated into the patch 102 can be configured such that they emit green light 117a from the patch 102 so as to be indicative of changes in pH of a growth medium. In some embodiments, emitted light 117a of a certain wavelength (e.g., green light) can be generated when the pH level is below or above a threshold level. As another example, chemicals impregnated into the patch 102 can be configured such that emitted light 117b of a certain wavelength (e.g., red light) from the patch 102 can be generated so as to be indicative of changes in DO of a growth medium. In some embodiments, emitted red light 117b can be generated when the DO level is below or above a threshold level. Thus, a first emitted light 117a of a certain wavelength can be generated that is indicative of pH level, and a second emitted light 117b of a certain wavelength can be generated that is indicative of DO level.

An example of a DO patch 102 can include a use of ruthenium-based oxygen sensing films such as Ru(II) tris (4,7-diphenyl-1,10-phenanthroline) complex, immobilized in a silicone rubber membrane (Bambot, S. B. et al., Biotechnol. Bioeng. 43: 1139-1145 (1994)). Another example of a DO patch 102 can include impregnating a material with an indicator dye such as a porphyrin dye, for example, or a metalloporphyrin such as platinum(II)-octaethyl-porphyrin combined with, e.g., encapsulated within, a polymer matrix such as polystyrene. The matrix layer may then be applied to a polystyrene support using, for example a toluene-based solvent (Liebsch, G. I. et al., Appl. Spectroscopy 54: 548-559 (2000)).

An example of a pH patch 102 can include impregnating a material with any known ratiometric pH sensitive dye, such as 1-hydroxypyrene-3,5,7-sulfonic acid (HPTS). A sterilized solution of the dye can be directly introduced into a bioreactor medium and detected via fluorescence. Fluorescence detection can be determined using front face geometry. For example, HPTS has two excitation peaks-400 and 450 nm. When excited at either 400 or 450 nm, HPTS can emit light at approximately 520 nm. The longer excitation peak can be excited using a blue LED (460 nm), for example, and the shorter excitation peak can be excited using an UV LED (375 nm), for example. The intensity ratio of the 520 nm fluorescence emissions from excitation at each of the two excitation peaks can be affected by the pH of the medium. Thus, the pH can be calibrated by measuring the intensity ratio of the 520 nm fluorescence emissions at each of the two excitation peaks as the pH changes. pH can be optionally verified on a benchtop pH meter. This ratiometric approach may avoid interference from turbidity changes and provides accurate measurements of pH.

Other examples of pH and DO patches 102 can be based on techniques disclosed in U.S. Pat. No. 6,673,532, filed Aug. 14, 2001, titled "Bioreactor and Bioprocessing Technique," which is incorporated herein by reference in its entirety.

Emitted light 117a, 117b from the patch 102 can travel back through the reaction vessel window 122 and further through the beam combiner assembly window 128. The emitted light 117a, 117b can be further directed to be incident upon the first filter/mirror arrangement 116a. It is contemplated for the emitted light 117a, 117b (e.g., light emitted due to fluorescence) to be generally at a wavelength that is higher than a wavelength of any of the excitation light beams 115a, 115b required to elicit the fluorescence effect. Thus, emitted light traveling 117a, 117b back toward the first filter/mirror arrangement 116a may have wavelengths that are greater than both of the first and second excitation light beams 115a, 115b. In at least one embodiment, a surface of first filter/mirror arrangement 116a can be configured to reflect the combined excitation light beams 119, but to pass emitted light beams 117a, 117b. For example, the surface of the first filter/mirror arrangement 116a can be configured to pass emitted red and/or green light coming in-through the beam combiner assembly window 128, but reflect combined violet-blue light beams so as to be directed out-through the beam combiner assembly window 128.

The emitted light 117a, 117b can be further directed to be incident upon a second filter/mirror arrangement 116b. As shown in FIG. 1, a pass filter can be generated by both the first filter/mirror arrangement 116a and the second filter/mirror arrangement 116b. In some embodiments the pass filter can be a long pass filter. The long pass filter can be configured for passing light with certain wavelengths, or light with wavelengths greater than a minimum wavelength. For example, with the violet and blue excitation light beams 115a, 115b and the green and red emitted light beams 117a, 117b, the long pass filter may be configured to pass light with wavelengths greater than 525 nm. The long pass filter can be used by the beam combiner assembly 104 to block any light below the minimum wavelength defined by the pass filter. For example, the long pass filter can be used by the beam combiner assembly 104 to block light that is at and/or below a wavelength of the emitted light 115a, 115b. This may be done to prevent any stray excitation light 115a, 115b from passing through the long pass filter, which may be used to prevent any excitation light 115a, 115b from being detected by the detector 124. For instance, the long pass filter can be used by the beam combiner assembly 104 to block any light having a wavelength that is at and/or below 525 nm (e.g., block the violet and/or blue excitation light), but allow passage of any emitted light 117a, 117b (e.g., allow the green and/or red emitted light). Emitted light 117a, 117b can then be directed to be incident upon the detector 124. Data signals from the detector 124 may then be used to record wavelengths and/or intensities of the emitted light 117a, 117b. The recorded wavelengths and/or intensities can be associated with changes in pH and/or DO levels. For example, wavelengths at and/or near the first emitted light 117a (e.g., the green light) can be indicative of a pH level at a threshold level and/or a decreasing pH level. Wavelengths at and/or near the second emitted light 117b (e.g., the red visible light) can be indicative of DO levels at a threshold level and/or increasing DO levels. Intensities of emitted light 117a, 117b can be indicative of an amount of pH and/or DO. Recording intensities as a function of time can be used to determine or calculate rates of change of pH level and/or DO level.

While various embodiments disclose use of two excitation light beams 115a, 115b and two emitted light beams 117a, 117b, these are one exemplary. There can be any number of excitation 115 and emitted light beams 117 used. Further, the excitation 115 and emitted light beams 117 are not limited to the specific wavelengths disclosed, but the specific wavelengths are only exemplary of what can be used.

The patch 102 can be a fluorescent-based optical patch. In one embodiment, the patch 102 can include a substrate with a polymeric backing. The substrate can be filter paper, which may be a monomer (e.g., methyl methacrylate) or cellulose-based filter paper. In some embodiments, the backing can include a silicon-based backing. The backings and/or the substrate can be configured to facilitate quick absorption of the excitation light beams 115a, 115b and quick radiation of emitted light beams 117a, 117b. One way to achieve this is by combining at least two fluorescent dyes in a monomer while depositing a measured amount of the same onto an inner surface of the reaction vessel 112. The measured amount can also be polymerized. It should be noted that the water solubility of polymers may vary, and thus polymer selection for the backing may be difficult. It should be further noted that the activity of chemical constituents of polymers can vary widely. Because of this potential variability, pre-calibration of the fluorescent response of a polymetric spot can be difficult to perform. However, using filter paper as a matrix for the reactive chemicals and dyes can facilitate easier calibration. Using filter paper as a matrix for the reactive chemicals and dyes can further increase the rate at which a response may be generated.

In one exemplary embodiment, a sterile optical patch 102 can be placed aseptically in the reaction vessel 112. The back of the patch 102 can be coated with an adhesive for adhering it to an inside surface of the reaction vessel 112. The adhesive can be a biocompatible adhesive. For example, silicone based adhesives with no support binders have been shown to be biocompatible. The patch 102 can be placed within the reaction vessel 112 so as to enable at least one excitation light beam 115a, 115b generated from the beam combiner assembly 104 to be incident upon it through a transparent portion of a reaction vessel 112. For example, the patch 102 can be placed adjacent the reaction vessel optical window 122 and/or at a position covering the reaction vessel optical window 122. In one embodiment, the patch 102 can be placed at a position subtending the reaction vessel optical window 122.

The transparent portion of the reaction vessel 112 can be the optical window 122 of the reaction vessel 112 configured to allow at least certain wavelengths of light (e.g., wavelengths associated with excitation light beams 115a, 115b and/or emitted light beams 117a, 117b) to transmit there-through. This may include blocking all other light from passing there-through, or blocking certain bands of light (wavelength bands). The patch 102 can include chemicals configured to generate at least one emitted light beam 117 when caused to fluoresce due to at least one excitation light beam 115 being incident upon it. This can be achieved by, for example, impregnating the patch 102 with a blend of chemicals to generate emitted light 117 when subjected to at least one excitation light beam 115 and/or a combined light beam 119 of at least two excitation beams 115. Chemicals within the patch 102 can be further configured to radiate at least one the emitted light 117 in response to changes in oxygen partial pressure and/or pH levels. In some embodiments, the patch 102 can be at least one of a pH patch and a DO patch. A pH patch can be configured to radiate emitted light 117 at a certain wavelength in response to changes in pH levels. A DO patch can be configured to radiate emitted light 117 at a certain wavelength in response to changes in DO levels.

The pH patch can be structured to generate a ratio-metric response. For example, the chemicals impregnated into the pH patch may be excited by two different, but close, excitation light beams 117 (e.g., different with respect to wavelengths). This can cause generation of two different emission light beams 117 (e.g., each having a different wavelength). Each wavelength of the different emitted light beams 117 can differ depending on changes in pH levels the pH patch is exposed to. The ratio between wavelengths of the different emission light beams 117 can be used as an indicator of the pH level of a growth media in the reaction vessel 112.

The DO patch can be a fluorescent oxygen-sensing patch, which can be structured to use oxygen as a quenching agent to quench a chemical response of chemicals impregnated into the DO patch while exposed to a presence of oxygen. The DO patch can be further structured to radiate emitted light when excited by a single excitation light beam 117. The DO patch can be further structured to generate an emitted light beam 117 as a function of the chemical response. In some embodiments, the DO patch can be structured such that the more oxygen that is present in the environment within which the DO patch is located, the less the chemical response occurs. This may lead to a weaker emission light beam signal. Thus, the less oxygen that is present, the greater the chemical response occurs. This may lead to a stronger emission light beam signal generated by the system 100. Thus, the lower the levels of DO within a culture sample, the stronger the signal that can be detected from the emitted light. Generally, oxygen content of the growth media in a culture growth bioprocess is less than that of ambient air. Therefore, enabling generation of strong signals in environments where oxygen content is within a range from greater than 0% to 21% can be beneficial for cell culture monitoring.

The detection system 100 can be configured so that a wavelength of an excitation light 115a beam to elicit a fluorescence response from a DO patch can be lower than a wavelength of an excitation light beam 115b to elicit a fluorescence response from a pH patch. For example, a wavelength of an excitation light beam 115a to elicit a response from a pH patch can be blue light beam (e.g., at or near 470 nm) and a wavelength of an excitation light beam 115b to elicit a response from a DO patch can be violet light beam (e.g., at or near 405 nm).

A mini-fluorometer can be used to generate excitation light beams 115a, 115b and to detect wavelengths of emitted light 117a, 117b. For example, the mini-fluorometer can be built into an integrated circuit board 134, which can be placed into communication with the computer device 110 via a hub box 118. Optoelectronics, such as a photodiode (e.g., the detector 124) for example, can be used to interrogate the patch 102 via modulation of excitation light beams 115a, 115b to detect the emitted light 117a, 117b. In some embodiments, a mini-fluorometer can be built into an integrated circuit board 134, both of which can be attached to and/or placed within the casing 126 forming the beam combiner assembly 104.

In at least one embodiment, an illumination source 114 for generating at least one excitation light beam 115 can be an LED. A band filter can be used to produce a narrow bandwidth of excitation light 115 coming from the illumination source 114. The band filter can be further used so that the gain of an LED may be adjusted to generate a desired intensity.

The patch 102 can be mediated by changes in pH levels and/or changes in DO levels in growth media that support growth of cells within the reaction vessel 112. Detected emitted light 117 radiating from the patch 102 can be captured as signals and digitized by the detector 124. The digitized signals can be transmitted as reaction vessel data to the computer device 110. The computer device 110 can be located within and/or outside of a bio-safety laboratory. With reaction vessel data, the computer device 110 can be programmed to calculate fluorescence lifetimes and decay rates associated with oxygen concentration. This can be done to calculate DO concentration within a growth medium of cell culture sample. A first user interface 132' can be displayed on the computer device 110, which may be programmed to cause the computer device 110 to display instantaneous values of DO concentration. (See FIG. 8A). A second user interface 132" can be programmed to cause the computer device 110 to display a time course of the calculated DO concentration and/or pH levels. For example, FIG. 8B shows time source data of pH units between 5.50 and 8.50.

The computer device 110 can be programmed to influence electrical, mechanical, and optical components of a detection system 100. This may include, but is not limited to, influencing controlling valves, pumps, mixers, detection devices, etc. For example, software can be stored on the memory 146a, 146b of the computer device 110, which may be programmed to cause the computer device 110 to accept reaction vessel data and/or to accept command data from users via the user interface 132', 132". Command data can include threshold levels and operating parameters. The software can be further programmed cause the computer device 110 to drive components of the detection system 100 automatically within user-defined thresholds and user-defined parameters. In addition, a user can set pre-established rules to influence threshold levels and operating parameters to generate variations within each reaction vessel 112. In some embodiments, the detection system 100 can be configured so that each reaction vessel 112 only responds to one set of parameters and thresholds, each of which can be pre-determined by a user. Thus, a group of parameters and thresholds can be set for a plurality of reaction vessels 112. For example, a group of parameters and thresholds can be set for as many as twelve reaction vessels 112. Any of the reaction vessels 112 can be arranged in parallel with another reaction vessel 112.

Some embodiments can include use of firmware as an alternative or in addition to software. In at least one embodiment, a digital sensing board ("DSB") in connection with the detection system 100 can include firmware programmed such that at least one computation is performed on the DSB. This can be done to have the DSB perform certain calculations and/or functions (e.g., addition of a gas to the reaction vessel 112) as opposed to the computer device 110 running software performing that calculation and/or function. In at least one embodiment, the DSB can be incorporated into a bioprocessor so that a signal can be transmitted from the DSB to a pump, a valve, or other system component. The signal can be transmitted directly from the DSB to the system component. Thus, actions performed by the system component can be initiated by the DSB and/or the computer device 100. In some embodiments, certain actions by the system component can be initiated by the DSB without being initiated by the software. This may be done to eliminate use of a computer device 110 for some or all aspects of the detection system 100. In some embodiment, monitoring functions and/or initiated action by certain monitoring functions can be customized by use of the software.

In at least one embodiment, the combined excitation light beam 119 can be collimated and coaxial. Further, the patch 102 can be placed adjacent the beam combiner assembly 104 so that it is subtending the detector 124. The beam combiner assembly 104 may be structured to combine at least two different excitation light beams 115. The beam combiner assembly 104 can be further structured to compare two emitted light 117 waves for pH analysis, and use intensity of a third emitted light 117 wave for DO analysis. The detection system 100 can be further configured to detect emitted light 117 with reference to an expected offset. This may allow use of the system 100 without a user knowing and/or without a user having to pre-setting the detection system 100 to accommodate: 1) which excitation light beams 115 are being generated and/or which emitted light beams 117 are being induced; 2) whether the patch 102 is a pH patch or a DO patch; and/or, 3) whether the reaction vessel 112 with both a pH patch and a DO patch is being used. Hence, a reaction vessel 112 containing a pH patch and/or a reaction vessel 112 containing a DO patch can be used at any time without having to calibrate and/or re-calibrate the detection system 100.

Referring to FIGS. 3-7, various views of exemplary beam combiner assemblies 104 are disclosed. In at least one embodiment, the beam combiner assembly 104 can include an array of four dichroic filter/mirrors within a circuit board block 134 as part of the pass filter. Some embodiments can include circuit board blocks 134 with a single detector 124 or single sensing unit (see FIGS. 3A-C) and some embodiments can include circuit board blocks 134' with a plurality of detectors 124 or a plurality of sensing units (see FIG. 3D-F).

Setting a filter/mirror within a base 135 of a circuit board 134 and shifting a mirror of a filter/mirror arrangement 116 can increase available space within the circuit board block 134, which can enable improvements within the detection system 100. Referring to FIGS. 4A-4B, shifting the mirror 160 of at least one filter/mirror assembly 116 can increase the available space within the circuit board block 134. Shifting the mirror 160 can also cause coincidence with an optical axis 170. For instance, FIG. 4B shows the mirror 160 that is configured to reflect the combined light beam 119 through the beam combiner assembly window 128 where the mirror 160 is shifted so that the reflected combined light 119 coincides with the optical axis 170 of beam combiner assembly window 128. In contrast, FIG. 4A shows an un-shifted mirror 160 that reflects the combined light beam 119 so that only a portion of the combined light 119 is transmitted through the beam combiner assembly window 128.

FIGS. 5A-5B show the reduction in space of the circuit board block 134 that may also be achieved with use of a cylindrical shaped filter/mirror 137. Setting the filter/mirror within the base 135 of the circuit board 134 can be achieved with use of a cylindrical shaped filter/mirror 137. Cylindrical shaped filters/mirrors 137 may not only reduce space within the circuit board block 134, but they can also be easier and less costly to set within the circuit board block 134 from a manufacturing stand-point than other shaped filters/mirrors. Thus, the cylindrical shape of the filter 137 can make it easier to set it into the circuit board 134, especially during mass production. FIG. 5A shows a circuit board block 134 with a non-cylindrical shaped filter/mirror. FIG. 5B shows an embodiment of the circuit board block 134 with the cylindrical shaped filter/mirror 137. With the exemplary embodiment of FIGS. 5A-5B, a reduction of 2.4 mm can be achieved via use of the cylindrical shaped filter/mirror 137. The reduction may be achieved by allowing the cylindrical filter/mirror 137 to extend at least partially into the base 135 of the circuit board block 134.

In at least one embodiment, the system 100 can include a filter/mirror arrangement 116 with a shifted mirror, where shifting the mirror can facilitate use of the cylindrical filter 137. In some embodiments, the shifted mirror 160 configuration can further allow the cylindrical filter 137 to protrude into the base 135 of the circuit board block 134 to which it may be attached. In some embodiments, the cylindrical filter 137 may extend below the base 135. This may enable reducing a height of the circuit board 134 even further, which may created additional room at the top of the circuit board 134. Reducing space can be beneficial, because the detection system 100 and/or the reaction vessel 112 may be placed within an incubator. The space within an incubator may be compromising, and thus a reduction in volume occupied by the detection system 100 can be beneficial.

Referring to FIGS. 6A-G, in some embodiments, increasing available space within the circuit board block 134 can facilitate placement of an offset-setting LED inside the circuit board block 134. As described earlier, an expected offset can be determined with use of a red reflector and/or a red LED. Any one of these may be referred to as an offsetting generator 180. In other words, the red reflector and/or the LED can be used to facilitate determining an expected offset by generating a light beam with a wavelength corresponding to the expected offset. The LED can be used as an alternative to the reflector or in addition to the reflector. Creating available space can facilitate placing the LED and/or reflector inside of the casing 126. Note that the LED and/or reflector can be any color LED or reflector that may correspond to the wavelength of light associated with the expected offset. Thus, the LED or reflector need not be a red.

Determining an expected offset can be achieved as follows. An empty reaction vessel 112 can be examined via the detection system 100. The red reflector can be placed against the beam combiner assembly window 128 so that red light can be detected by the detection system 100. Alternatively, a red LED can be included within the circuit board block 134 of the beam combiner assembly 104. The beam combiner assembly 104 can generate excitation light beams 115 so as to detect red light by the detector 124, the red light being generated by the offsetting generator 180. This detected red light can be used as an expected offset. As noted above, the offset generator need not be red, but the detected red light can be used as an expected offset with embodiments where the presence of DO is expected to radiate red light by a DO patch. It should be noted that the chemical response for a DO patch can be linear. Thus, the red light of the red LED or red reflector can simulate the expected red emitted light of a DO patch when in use within the reaction vessel 112 and when DO is present within the reaction vessel 112.

Using an expected offset can enable use of any reaction vessel 112 without knowing beforehand whether the reaction vessel 112 has a pH patch or a DO patch. This can further enable use of the detection system 100 without performing calibration of filter/mirror positions and/or angles. For example, the detection system 100 can be encoded with the expected offset before using any patch 102 to conduct monitoring (e.g., the expected offset can be encoded to be used by software operated by the computer device 110). During use with the patch 102, the detection system 100 can detect emitted light 117, and if the emitted light 117 is at or near the expected red light (i.e., the expected offset) then the detection system 100 can automatically determine that a DO patch is being used. If during use with the patch 102, the detection system 100 detects emitted light 117 that is not at or near the expected offset, then the detection system 100 can automatically determine that a pH patch is being used. The expected offset can be determined for each patch 102, or a set of patches 102, and encoded to be associated with each patch 102, or set of patches 102. Each patch 102, or set of patches 102, can be associated with the expected offset before being used in a detection system 100 for monitoring cell cultures.

In at least one embodiment, the detection system 100 can be used in the following manner. An empty reaction vessel 112 without the patch 102 can be placed inline with an excitation path of the system 100 such that there is no reflected (fluoresced) light reaching the detector 124. The red reflector 180 can be placed against a beam combiner assembly window 128. Alternatively, a red LED 180 can be included within the circuit board block 134 of the beam combiner assembly 104. The reaction vessel 112 can then be placed adjacent the beam combiner assembly 104 so as to be between the beam combiner assembly 104 and the red reflector 180 and/or red LED 180. The beam combiner assembly 104 can be caused to generate excitation light beams 115 so as to detect red light by the detector 124, the red light being generated by the reflector offsetting generator 180. Alternatively, the LED offsetting generator 180 can be used to generate the red light. The detected red light can be used to determine an expected offset. The expected offset can then be record. The recorded expected offset can be associated with a plurality of patches 102, the plurality including at least one of a pH patch and a DO patch, so that an expected offset can be known for users of a set of patches 102. The expected offset associated with each patch 102 and/or set of patches 102 can be recorded and coded. A coded expected offset associated with each patch 102 and/or set of patches 102 can be placed within a barcode associated (e.g., attached thereto) with the reaction vessel 112 and/or patch 112, stored as a scatter code, stored within software of the computer device 102, transmitted to the computer device 102 from another computer device 102 via the computer system 106, etc.

A pH patch and/or a DO patch can be affixed to an inside of the reaction vessel 112 with the reaction vessel 112 being empty otherwise. A cell culture sample can be placed within the reaction vessel 112 for which an expected offset for the patch 102 associated therewith has been calculated. The red reflector offsetting generator 180 can be removed from a beam combiner assembly 104 and/or the red LED offsetting generator 180 can be turned off. At least one of a violet excitation light beam 115a (e.g., at or near 405 nm) and a blue excitation light beam 115b (e.g., at or near 470 nm) can be generated to be combined into a combined violet-blue excitation light beam 119 by the beam combiner 130. The combined violet-blue excitation light beam 119 can include the combined violet excitation light beam 115a and a blue excitation light beam 115b, which may be combined to be collimated and coaxial. The combined violet-blue excitation light beam 119 can be directed through the beam combiner assembly window 128 and further through the reaction vessel window 122 to be incident upon at least one of a pH patch and a DO patch. The combined violet-blue excitation light beam 119 can induce fluorescence from chemicals within at least one of the pH patch and the DO patch so that emitted light 117a, 117b is radiated therefrom and directed back through the reaction vessel window 122 and further through the beam combiner assembly window 128 to be incident upon the pass filter. The pass filter can pass light with wavelengths at or greater than 525 nm so as to be incident upon the detector 124, but block light with wavelengths less than 525 nm.

The detector 124 can digitize the emitted light 117a, 117b being incident upon it. The detector 124 can also record at least one of wavelength and intensity of the emitted light. The detector 124 can also be configured for generating a representative data detection signal therefrom. The detection signal can be transmitted to the hub box 118. The hub box 118 can be in communication with at least one beam combiner assembly 104, which can be in further communication with at least one computer device 102 (see FIG. 1B). The coded expected offset for the reaction vessel 112 and/or patch 102 can be entered into the computer device 102 for the reaction vessel 112 and/or a patch 102 or a set of reaction vessels 112 and/or set of patches 102. The computer device 110 can then process, manipulate, and store detection signals for monitoring conditions of the cell growth medium of a cell culture within each reaction vessel 112 transmitting data to the detection system 100.

If during detection of emitted light 117a, 117b, an expected offset is detected, the computer device 110 can be programmed to determine that a DO patch is being used, a threshold level of DO is present, and/or a DO level is increasing or decreasing. If during detection of emitted light 117a, 117b, no expected offset is detected, the computer device 110 can be programmed to determine that a pH patch is being used, a threshold level of pH is present, and/or a pH level is increasing or decreasing. The reaction vessel 112 can be removed from the beam combiner assembly 104 and a different reaction vessel 112 can be placed on the beam combiner assembly 104 for DO level and pH level monitoring without calibration of filter/mirror positions and/or angles.

The reaction vessel 112 using the patch 102 from a same set can be switched multiple of times without calibration of filter/mirror position and/or angle and without entering a coded expected offset. If a reaction vessel 112 from a different set is used, monitoring can be done without calibration of filter/mirror positioning and/or angle, but a coded expected offset associated with those set of patches 102 and/or reaction vessels 112 may have to be entered.

Figure 9A:
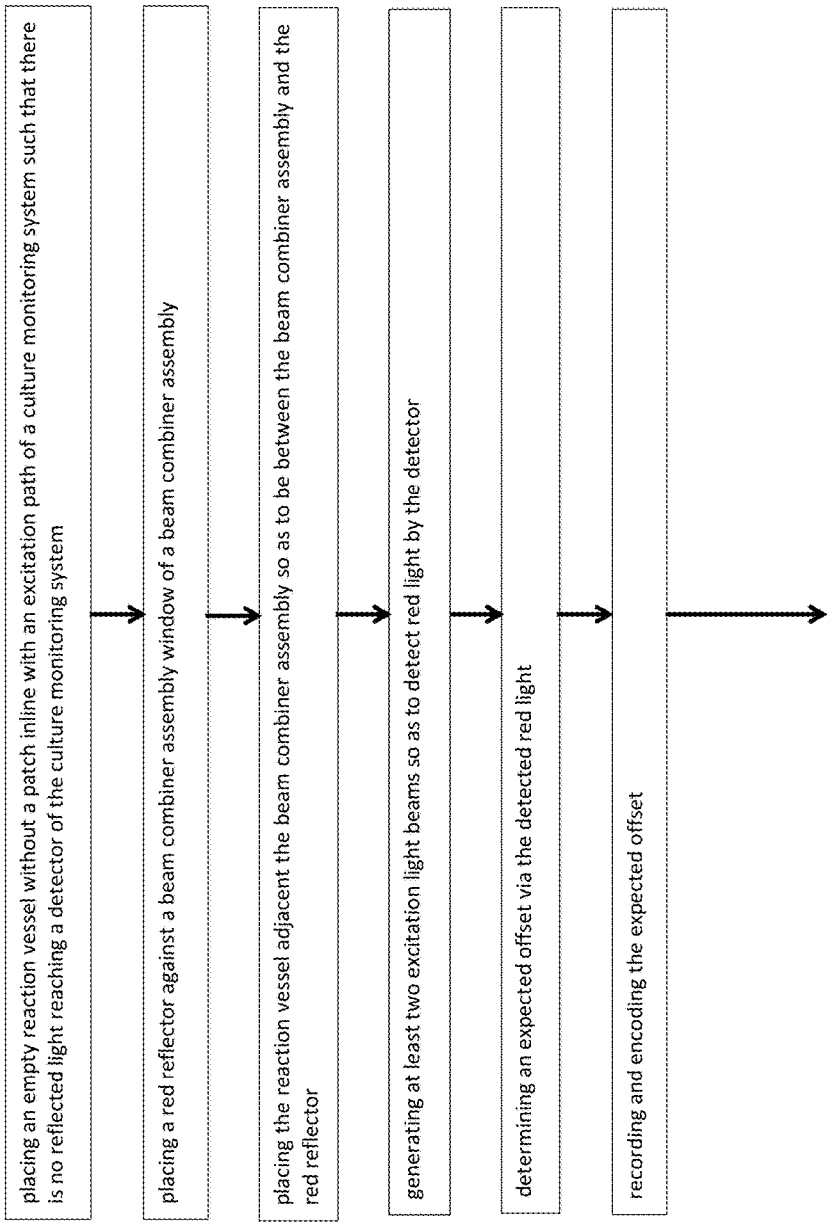
FIGS. 9A-9B show an exemplary method of using an embodiment of the detection system. Note that FIG. 9B is a continuation of the process that begins on FIG. 9A.
Figure 9B:
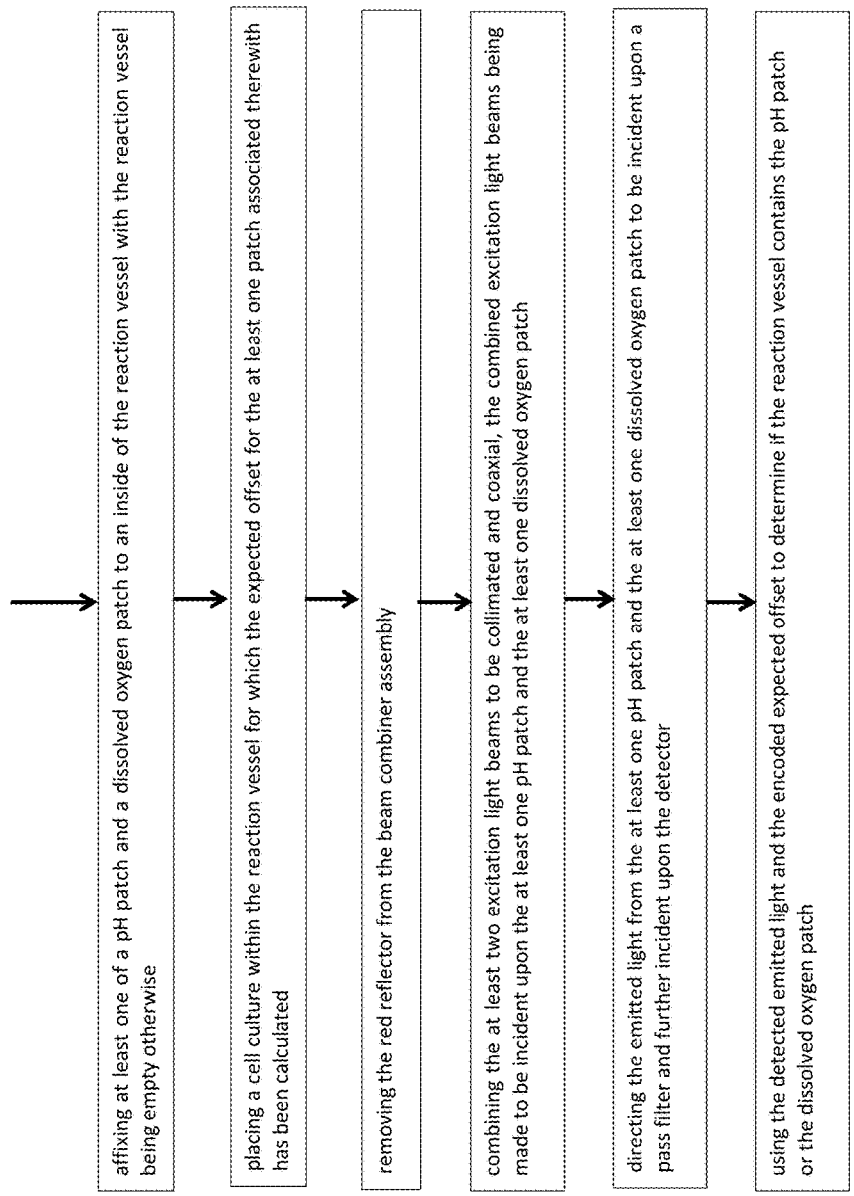

Referring to FIGS. 9A-B, a method of using the detection system 100 can include monitoring cell cultures. The method can include placing an empty reaction vessel 112 without a patch 102 inline with an excitation path of a culture monitoring system such that there is no reflected light reaching the detector 124 of the culture monitoring system. The method can further include placing a red reflector offsetting generator 180 against a beam combiner assembly window 128 of a beam combiner assembly 104. The method can further include placing the reaction vessel 112 adjacent the beam combiner assembly 104 so as to be between the beam combiner assembly 104 and the red reflector offsetting generator 180. The method can further include generating at least two excitation light beams 115a, 115b so as to detect red light by the detector 124, the red light being generated by the red reflector offsetting generator 180. The method can further include determining an expected offset via the detected red light. The method can further include recording and encoding the expected offset. The method can further include affixing at least one of a pH patch 102 and a dissolved oxygen patch 102 to an inside of the reaction vessel 112 with the reaction vessel 112 being empty otherwise. The method can further include placing a cell culture within the reaction vessel 112 for which the expected offset for the at least one patch associated therewith has been calculated. The method can further include removing the red reflector offsetting generator 180 from the beam combiner assembly 104. The method can further include combining the at least two excitation light beams 115a, 115b to be collimated and coaxial, the combined excitation light beams 119 being made to be incident upon the at least one pH patch 102 and the at least one dissolved oxygen patch 102. The method can further include directing the emitted light 117a, 117b from the at least one pH patch 102 and the at least one dissolved oxygen patch 102 to be incident upon a pass filter and further incident upon the detector 124. The method can further include using the detected emitted light and the encoded expected offset to determine if the reaction vessel 112 contains the pH patch 102 or the dissolved oxygen patch 102.

Figure 8A:
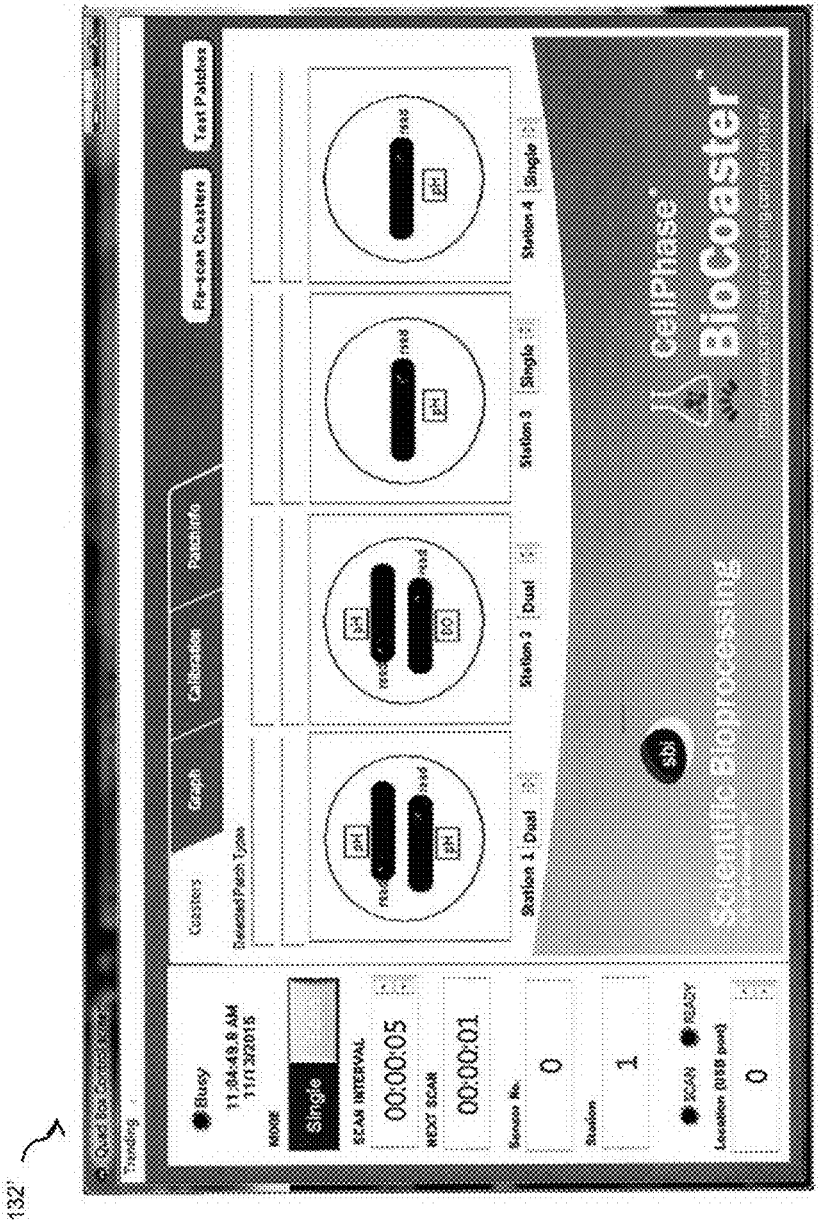
FIGS. 8A and 8B are an exemplary user interfaces that may be displayed on a computer device that can be used with an embodiment of detection system.
Figure 8B:
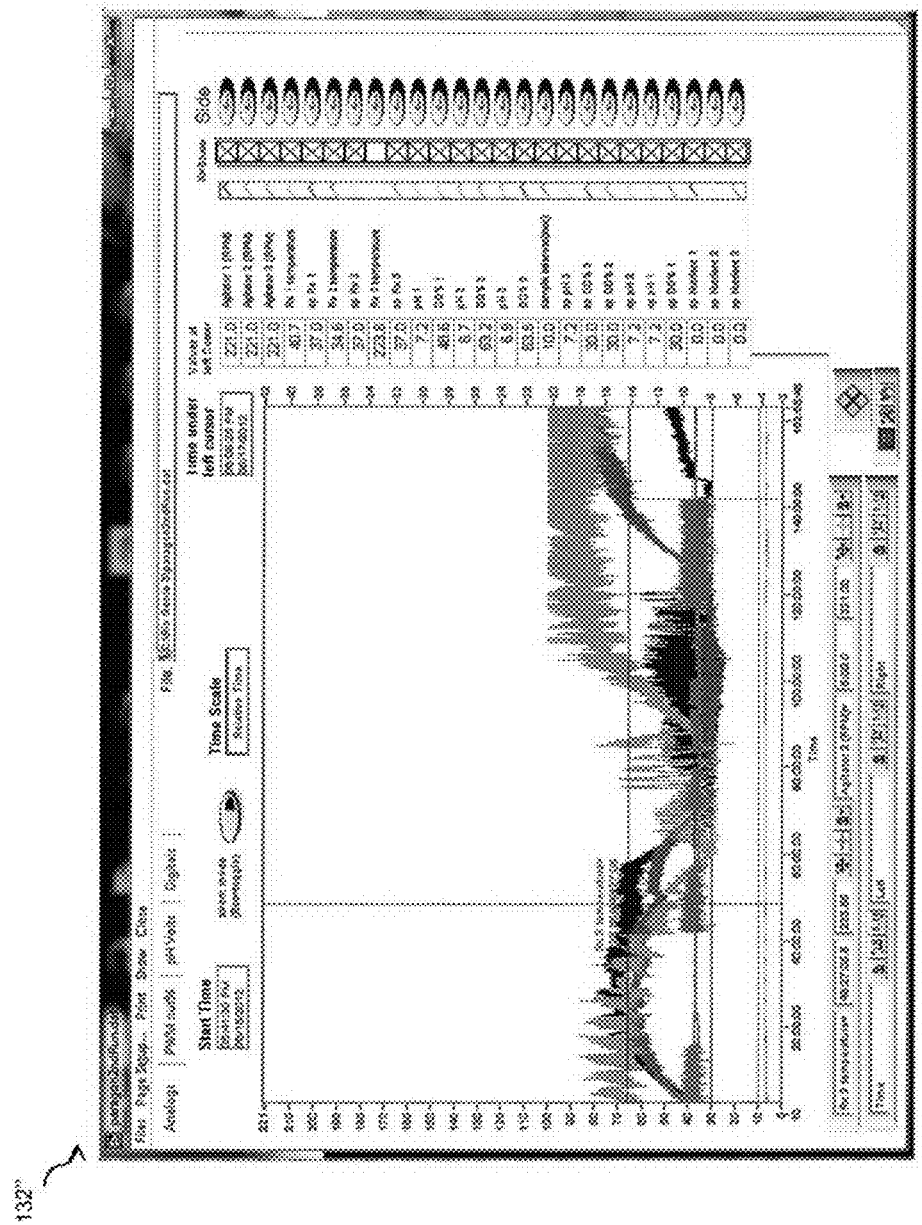
Figure 10:
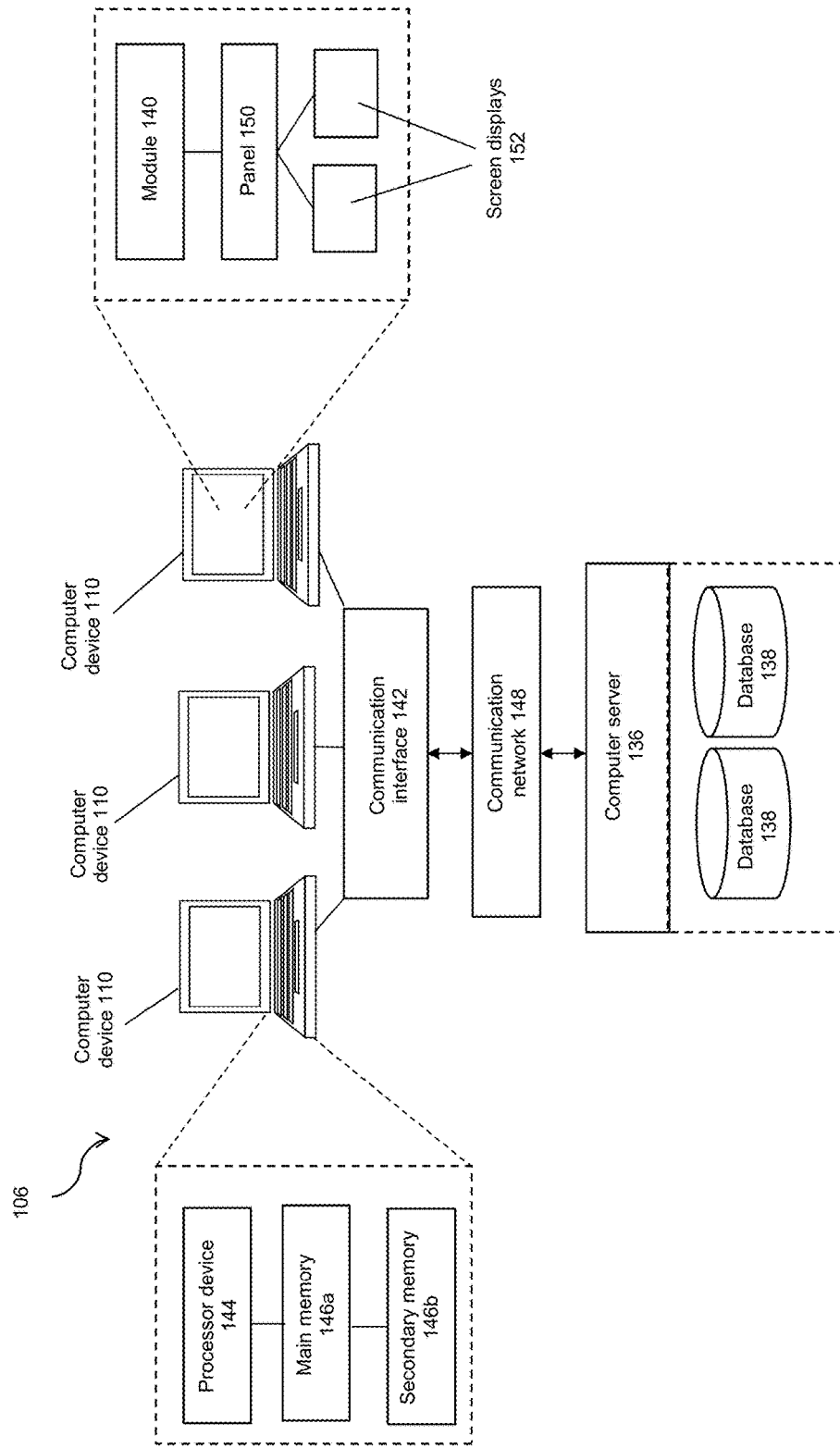
FIG. 10 is an exemplary computer system that may be used with a detection system.

In further embodiments, a feedback loop can be generated via the detection system 100 and at least one computer device 110 so that reaction vessel data can be transmitted to the computer device 110 and command data can be to be transmitted to at least one beam combiner assembly 104 from a user of the computer device 110 via the user interfaces 132', 132" of the detection system 100 (see FIGS. 8A-8B and 10). Furthermore, controllers and actuators can be used to influence pumps, photodiodes, etc. of the detection system 100 via command data transmitted through the computer device 110 and/or the DSB. The computer device 110 and/or DSB can be programmed to generate command data automatically based on algorithms, which can be based on reaction vessel data being collected. Additionally, or in the alternative, command data can be entered by a user via the user interface 132', 132" of the computer device 110 in communication with the detection system 100.

Exemplary Computer System Architecture

As shown in FIGS. 8A-8B and 10, detection system 100 can include a computer system 106 programmed to generate at least one user interface ("UI") 132', 132" displayed on a display unit of at least one computer device 110. Data entered via a module of the UI 134 can be transmitted to the computer system 106 for processing and storage Data acquisitioned from a detection system 100, a database of the computer system 106, and/or any other computer device 110 of the computer system 106 may be transmitted to the computer system 106 to be manipulated by a processor device for generating functional aspects of various user interfaces 132', 132' that can be displayed by any of the computer devices 110 in communication with the detection system 100. Wherever a user is referenced in this disclosure, it is understood that this reference includes computer device(s) 110, computer server(s) 136, and/or database(s) 138 associated with the user's use thereof. Distributed communication networks used to enable connection and communication between each computer device 110 may include communications in whole, or in part, via web-sites through at least one communication network, which may include a web-server.

The computer system 106 may include a plurality of computer devices 110, computer servers 136, databases 138, communication networks 148, and/or communication path/connections. A user of the detection system 100 may use at least one processor device 144, memory storage 146a, 146b, and communications interface 142 to communicate and execute commands. Each computer server 136 may be connected to at least one database 138, where software executed by each computer device 110 may carry out functions of storing, coalescing, configuring, and/or transmitting data. Software may be stored on any type of suitable computer-readable medium or media. This may be a non-transitory computer-readable medium or media, such as a magnetic storage medium, optical storage medium, or the like.

The computer system 106 architecture shown in FIG. 10 is an exemplary embodiment of a computer system 106 that may be used to facilitate interactions between computer devices 110, at least one DSB, users of computer devices 110, and the computer system 106, which may be implemented using hardware, software, firmware, non-transitory computer readable media having instructions stored thereon, or any combination thereof, and may be implemented in a single or multiple of computer systems 106 or other processing systems. Hardware, software, or any combination thereof may embody software and/or hardware modules 140 and/or components used to execute functions of the computer system 106 and/or detection system 100. If programmable logic is used, such logic may execute on a processing platform or a special purpose device. Embodiments of the disclosed subject matter can be practiced by using various computer system configurations, including multi-core multiprocessor systems, minicomputers, mainframe computers, computers linked or clustered with distributed functions, and/or pervasive or miniature computers that may be embedded into virtually any device. For instance, the computer device 110 can include a processor device 144 operably associated with a memory 146a, 146b. Any computer device 110 may be used to implement any disclosed embodiment of the invention.

The processor device 144 may be a single processor, a plurality of processors, or combinations thereof. The processor device 144 may have one or more processor cores. The processor device 144 may be a special purpose or a general purpose processor device. The processor device 144 may be connected to a communication infrastructure. The communication infrastructure may include, but is not limited to, a bus, message queue, network, multi-core message-passing scheme, etc.

The computer device 110 may include a main memory 146a. The main memory 146a may include, but is not limited to, a random access memory, a read-only memory, etc. The computer device 110 may include a secondary memory 146b. The secondary memory 147b may include, but is not limited to, a hard disk drive, a removable storage drive, a floppy disk drive, a magnetic tape drive, an optical disk drive, a flash memory, etc. Any of the main and the secondary memories 146a, 146b can be a non-volatile memory.

Computer program medium, non-transitory computer readable medium, and computer usable medium may refer to tangible media, such as, for example, a removable storage unit and a hard disk installed in a hard disk drive. The removable storage drive may read from and/or write to a removable storage unit. The removable storage unit can include a removable storage media that can be read by, and written to, a removable storage drive. For example, if a removable storage drive is a floppy disk drive, the removable storage unit may be a floppy disk. The removable storage unit can also be non-transitory computer readable recording media.

In some embodiments, the secondary memory 146b may include alternative means for allowing computer programs or other instructions to be loaded into the computer device 110 and/or computer system 106. This may be, for example, a removable storage unit and/or an interface. Examples of such means may include, but are not limited to, a program cartridge and cartridge interface (e.g., as found in video game systems), a removable memory chip (e.g., Electronic Erasable Readable Programmable Read-Only Memory ("EEPROM"), Programmable Read-Only Memory ("PROM")), etc. and associated socket, and/or other removable storage units and interfaces.

The computer system 106 may include a communications interface 142. The communications interface 142 may be configured to allow software and data to be transferred between computer devices 110 within the computer system 106 and/or the computer system 106 and external devices. Communications interfaces 142 may include, but are not limited to, a modem, a network interface (e.g., an Ethernet card), a communications port, a Personal Computer Memory Card International Association ("PCMCIA") slot and card, etc. Software and data transferred via a communications interface may be in a form of signals, which may be electronic, electromagnetic, optical, or other signals. Signals may travel via a communications path, which may be configured to carry signals and may be implemented using wire, cable, fiber optics, a phone line, a cellular phone link, a radio frequency link, etc.

Computer program medium and computer usable medium may refer to memories, such as a main memory and a secondary memory, which may be memory semiconductors (e.g., Dynamic Random-Access Memory ("DRAM")). These computer program products may be means for providing software to the network. Computer programs (e.g., computer control logic) may be stored in a main memory 146a and/or a secondary memory 146b. Computer programs may also be received via the communications interface 142. Such computer programs, when executed by a processor device 144, may enable a computer device 110 to execute commands and act upon the various components of the system 106. Accordingly, such computer programs may represent controllers of the computer system 106, where software may be stored in a computer program product and loaded into the computer device 110 using a removable storage drive, an interface, a hard disk drive, and/or a communications interface 142.

In some embodiments, the computer device 110 include a processor, a microprocessor, minicomputer, server, mainframe, laptop, personal data assistant, a cellular phone, smartphone, pager, or any other programmable device configured to enable transmission and/or reception of data, which may be over a network. The computer device 110 may include a peripheral device, such as an input/output device. The peripheral device may include, but is not limited to, a keyboard, a mouse, a screen display, a touch screen, a stylus pen, a monitor, a printer, a hard disk drive, a floppy disk drive, a joystick, an image scanner, etc.

One or more electronic communication networks 148 may be utilized by the computer system 106 to promote communication among different components, transfer data, and/or share resource information. Such communication networks 148 may be embodied as, but not limited to, at least one of Ethernet, wireless Local Area Network ("LAN"), Mobile Area Network ("MAN"), Wide Area Network ("WAN"), Virtual Private Network ("VPN"), Storage Area Network ("SAN"), Global Accelerator Network ("GAN"), Home Phoneline Network Alliance ("HomePNA"), etc.

In some embodiments, the computer system 106 may include a computer device 110 configured as a processor 144 operatively associated with at least one module 140, which may be programmed to display panels 150 and/or screen displays 152 on a monitor of a computer device 110. The processor 144 may be programmed to execute computer-readable instructions included within the module 140. Computer-readable instructions may be in a form of software stored on a non-transitory computer readable medium operatively associated with the processor 144. Each module 140 may be configured to generate the user interface ("UI") 132', 132", which may enabling at least one user to issue commands, access data stored on a data storage media operatively associated with the processor, and/or transmit data to and from the data storage media. The module 140 may include software, firmware, hardware, or any reasonable combination thereof.

Any of the panels 150 may be programmed to display information and grant access to data related to certain aspects and functionalities of the computer system 106 and/or detection system 100. Through the various modules 140 and panels 150, the computer system 106 can provide a communication network to orchestrate interaction between a user, the computer system 106, and the various components of the detection system 100. For instance, different panels 150 of each module 140 may be programmed to facilitate differentiated display of information and differentiated interaction between users, components of a computer system, and components of the detection system 100. This may be achieved by each module 140 generating different UIs 132', 132" for control of different aspects of the detection system 100.

Various embodiments of the present disclosure can be described in terms of the example computer system 106 described herein; however, other embodiments of the computer system 106, along with other embodiments of computer architectures, can be used. Although operations may be described as a sequential process, some of the operations may be performed in parallel, concurrently, and/or in a distributed environment, and with program code stored locally or remotely for access by single or multi-processor machines.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A cell culture monitoring system, comprising:
   a reaction vessel;
   a beam combiner assembly configured to generate at least one excitation light beam for inducing fluorescence;
   at least one patch configured to be placed within the reaction vessel and to generate emitted light due to the induced fluorescence by the at least one excitation light beam; and,
   a detector to detect the emitted light;
   wherein:
   the at least one patch is associated with an expected offset, the expected offset being an expected wavelength of the emitted light corresponding to the at least one patch generating the emitted light while in presence of dissolved oxygen;
   the detector is configured to detect a wavelength of emitted light relative to the expected offset;
   a hub box in connection with the beam combiner assembly, the hub box configured to receive data representative of emitted light detected by the detector and to transmit the emitted light data to a computer device, the computer device configured to determine a type of the at least one patch based on the emitted light data and the expected offset.

2. The system recited in claim 1, wherein the at least one patch further comprises at least one of a pH patch and a dissolved oxygen patch, the pH patch being impregnated with chemicals to generate a first wavelength upon induced fluorescence and the dissolved oxygen patch being impregnated with chemicals to generate a second wavelength upon induced fluorescence, wherein an intensity of the emitted light from the dissolved oxygen patch increases as a level of dissolved oxygen concentration that the dissolved oxygen patch is exposed to decreases.

3. The system recited in claim 1, wherein the at least one patch comprises a cellulous-based filter paper with a silicon adhesive backing.

4. The system recited in claim 1, wherein the beam combiner assembly generates the at least one excitation light beam via a light emitting diode, wherein the beam combiner assembly further comprises a band filter to generate a bandwidth of excitation light.

5. The system recited in claim 1, wherein:
the beam combiner assembly further comprises at least one illumination source, a beam combiner, a first filter and mirror arrangement, a second filter and mirror arrangement, and the detector;
the at least one excitation light beam is sent through the beam combiner to be combined with another excitation light beam, the combined excitation light beam being collimated and coaxial, the combined excitation light beam being directed to be incident on the at least one patch within the reaction vessel;
the combined excitation light beam inducing the emitted light from the at least one patch due to induced fluorescence, the emitted light being incident upon the first filter and mirror arrangement and the second filter and mirror arrangement to be detected by the detector; and,
the beam combiner assembly being housed within a circuit board block, wherein a filter of at least one of the first filter and mirror arrangement and the second filter and mirror arrangement is seated within a base of the circuit board block, wherein a mirror of at least one of the first filter and mirror arrangement and the second filter and mirror arrangement is shifted with respect to its associated filter.

6. A cell culture monitoring system, comprising:
a reaction vessel comprising a patch placed within the reaction vessel;
a beam combiner assembly configured to generate at least two excitation light beams for inducing fluorescence, the beam combiner assembly comprising at least one illumination source, a beam combiner, a first filter and mirror arrangement, a second filter and mirror arrangement, and a detector;
wherein:
the at least two excitation light beams are combined by the beam combiner to be collimated and coaxial, the combined excitation light beam being directed to be incident on the patch a patch;
the combined excitation light beam induces emitted light from the patch due to induced fluorescence, wherein the emitted light is directed to be incident upon the first filter and mirror arrangement and the second filter and mirror arrangement to be detected by the detector;
the beam combiner assembly is housed within a circuit board block, wherein a filter of at least one of the first filter and mirror arrangement and the second filter and mirror arrangement is seated within a base of the circuit board block, wherein a mirror of at least one of the first filter and mirror arrangement and the second filter and mirror arrangement is shifted with respect to its associated filter;
the patch is associated with an expected offset, the expected offset being an expected wavelength of the emitted light corresponding to the patch generating the emitted light while in presence of dissolved oxygen;
the detector is configured to detect a wavelength of emitted light relative to the expected offset;
a hub box in connection with the beam combiner assembly, the hub box configured to receive data representative of emitted light detected by the detector and to transmit the emitted light data to a computer device, the computer device configured to determine a type of the patch based on the emitted light data and the expected offset.

7. The system recited in claim 6, wherein the patch further comprises at least one of a pH patch and a dissolved oxygen patch, the pH patch being impregnated with chemicals to generate a first wavelength upon induced fluorescence and the dissolved oxygen patch being impregnated with chemicals to generate a second wavelength upon induced fluorescence, wherein an intensity of the emitted light from the dissolved oxygen patch increases as a level of dissolved oxygen concentration that the dissolved oxygen patch is exposed to decreases.

8. The system recited in claim 6, wherein the patch comprises a cellulous-based filter paper with a silicon adhesive backing.

9. The system recited in claim 6, wherein the beam combiner assembly generates the at least two excitation light beams via at least one light emitting diode, wherein at least one band filter is used to generate a bandwidth of excitation light for each excitation light beam.

10. A method of monitoring cell cultures, the method comprising:
placing an empty reaction vessel without a patch inline with an excitation path of a culture monitoring system such that there is no reflected light reaching a detector of the culture monitoring system;
placing a red reflector against a beam combiner assembly window of a beam combiner assembly, the beam combiner assembly being configured to generate at least one excitation light beam for inducing fluorescence;
placing the reaction vessel adjacent the beam combiner assembly so as to be between the beam combiner assembly and the red reflector;
generating at least two excitation light beams so as to detect red light by the detector, the red light being generated by the red reflector;
determining an expected offset via the detected red light;
recording and encoding the expected offset;
affixing a pH patch or a dissolved oxygen patch to an inside of the reaction vessel with the reaction vessel being empty otherwise, the pH patch or the dissolved oxygen patch being configured to generate emitted light due to the induced fluorescence by the at least one excitation light beam;

placing a cell culture within the reaction vessel for which the expected offset for the pH patch or dissolved oxygen patch associated therewith has been calculated and encoded;

removing the red reflector from the beam combiner assembly;

combining the at least two excitation light beams to be collimated and coaxial, the combined excitation light beams being made to be incident upon the pH patch or the dissolved oxygen patch;

directing the emitted light from the pH patch or the dissolved oxygen patch to be incident upon a pass filter and further incident upon the detector, wherein the pH patch or the dissolved oxygen patch is associated with the expected offset so that an expected wavelength of the emitted light corresponding to the pH patch or the dissolved oxygen patch is emitted light while in presence of dissolved oxygen, wherein the detector is configured to detect a wavelength of emitted light relative to the expected offset;

using the detected emitted light and the encoded expected offset to determine if the reaction vessel contains the pH patch or the dissolved oxygen patch;

using a hub box in connection with the beam combiner assembly to receive data representative of emitted light detected by the detector and to transmit the emitted light data to a computer device;

using the computer device to determine a type of the pH patch or the dissolved oxygen patch based on the emitted light data and the expected offset.

11. The method recited in claim 10, further comprising using the detected emitted light and the encoded expected offset to determine the type of the pH patch or the dissolved oxygen patch for a plurality of pH patches or dissolved oxygen patches, creating a set of patches associated with an expected offset code.

12. The method recited in claim 10, further comprising generating the red light via a light emitting diode incorporated into the beam combiner assembly as opposed to using the red reflector.

13. The method recited in claim 10, further comprising monitoring the cell culture within the reaction vessel without calibration of filter angle and without calibration of filter positioning of a filter within the beam combiner assembly.

14. The method recited in claim 10, further comprising generating the at least two excitation light beams via at least one light emitting diode and generating a bandwidth of excitation light for the at least two excitation light beams.

15. The method recited in claim 14, further comprising adjusting a gain of the at least one light emitting diode, generating a specific intensity each for the at least two excitation light beams.

16. The method recited in claim 10, wherein the computer device is used to influence electrical, mechanical, and optical components of the culture monitoring system.

* * * * *